US012690995B2

(12) United States Patent
Paluszek et al.

(10) Patent No.: US 12,690,995 B2
(45) Date of Patent: Jul. 28, 2026

(54) ANTERIOR CRUCIATE LIGAMENT PROTECTOR

(71) Applicant: PRINCETON SATELLITE SYSTEMS, INC., Plainsboro, NJ (US)

(72) Inventors: Michael Paluszek, Plainsboro, NJ (US); Joyce Mo, Highland Park, NJ (US)

(73) Assignee: PRINCETON SATELLITE SYSTEMS, INC., Plainsboro, NJ (US)

( * ) Notice: Subject to any disclaimer, the term of this patent is extended or adjusted under 35 U.S.C. 154(b) by 0 days.

(21) Appl. No.: 19/092,886

(22) Filed: Mar. 27, 2025

(65) Prior Publication Data

US 2025/0302653 A1     Oct. 2, 2025

Related U.S. Application Data

(60) Provisional application No. 63/570,472, filed on Mar. 27, 2024.

(51) Int. Cl.
A61F 5/00          (2006.01)
A61B 5/00          (2006.01)
        (Continued)

(52) U.S. Cl.
CPC .......... A61F 5/0123 (2013.01); A61B 5/1123 (2013.01); A61B 5/389 (2021.01);
        (Continued)

(58) Field of Classification Search
CPC ..... A61F 5/0125; A61B 5/389; A61B 5/7264; A61B 5/486; A61B 5/1123; A61B 2505/09
See application file for complete search history.

(56) References Cited

U.S. PATENT DOCUMENTS

2021/0260371 A1*   8/2021   Shahriari ........... A61N 1/36021

OTHER PUBLICATIONS

Moghadam, S.M., Yeung, T. & Choisne, J. A comparison of machine learning models' accuracy in predicting lower-limb joints' kinematics, kinetics, and muscle forces from wearable sensors. Sci Rep 13, 5046 (2023). https://www.nature.com/articles/s41598-023-31906-z (Year: 2023).*

(Continued)

*Primary Examiner* — Kim M Lewis
(74) *Attorney, Agent, or Firm* — AddyHart

(57)                    ABSTRACT

A wearable knee brace system integrates inertial measurement unit (IMU) and electromyography (EMG) sensors with machine learning models to prevent anterior cruciate ligament (ACL) and posterior cruciate ligament (PCL) injuries. The system collects real-time biomechanical and neuromuscular data and analyzes the data using supervised, personalized, or federated learning techniques to identify high-risk movement patterns. Upon detecting elevated injury risk, the system may issue real-time alerts or activate a hybrid actuation system comprising high-force, low-displacement actuators and low-force, high-displacement actuators to reduce joint loading. The system further supports personalized model adaptation using calibration activities and transfer learning, as well as privacy-preserving performance improvements through federated learning. Feedback is provided through visual, auditory, or haptic interfaces and may be integrated with rehabilitation tools or mobile applications. The system may be used in athletic, dance, clinical, or rehabilitative environments to enhance performance, optimize recovery, and reduce the risk of knee ligament injuries.

20 Claims, 10 Drawing Sheets

(51) Int. Cl.
    *A61B 5/11*         (2006.01)
    *A61B 5/389*       (2021.01)
    *A61F 5/01*         (2006.01)

(52) U.S. Cl.
    CPC ............ *A61B 5/486* (2013.01); *A61B 5/7264*
        (2013.01); *A61B 5/7275* (2013.01); *A61B*
        *5/742* (2013.01); *A61B 2505/09* (2013.01);
        *A61B 2560/0238* (2013.01); *A61B 2562/0219*
        (2013.01); *A61F 2005/0132* (2013.01)

(56)            References Cited

OTHER PUBLICATIONS

Coker, C., Chen, H., Schall, M.C., Gallagher, S., Zabala, M. EMG and Joint Angle-Based Machine Learning to Predict Future Joint Angles at the Knee. Sensors 2021, 21(11), 3622 https://www.mdpi.com/1424-8220/21/11/3622 (Year: 2021).*

* cited by examiner

400

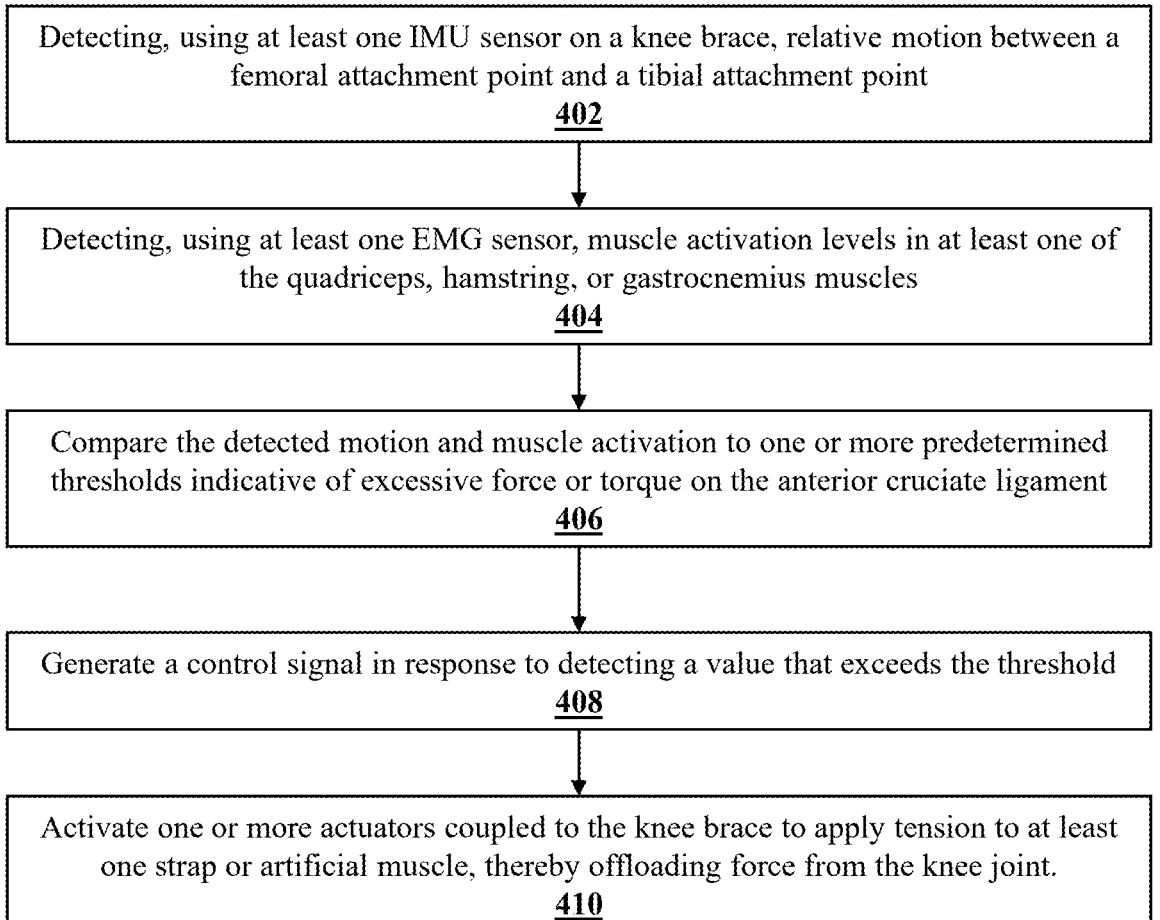

Detecting, using at least one IMU sensor on a knee brace, relative motion between a
femoral attachment point and a tibial attachment point
402

Detecting, using at least one EMG sensor, muscle activation levels in at least one of
the quadriceps, hamstring, or gastrocnemius muscles
404

Compare the detected motion and muscle activation to one or more predetermined
thresholds indicative of excessive force or torque on the anterior cruciate ligament
406

Generate a control signal in response to detecting a value that exceeds the threshold
408

Activate one or more actuators coupled to the knee brace to apply tension to at least
one strap or artificial muscle, thereby offloading force from the knee joint.
410

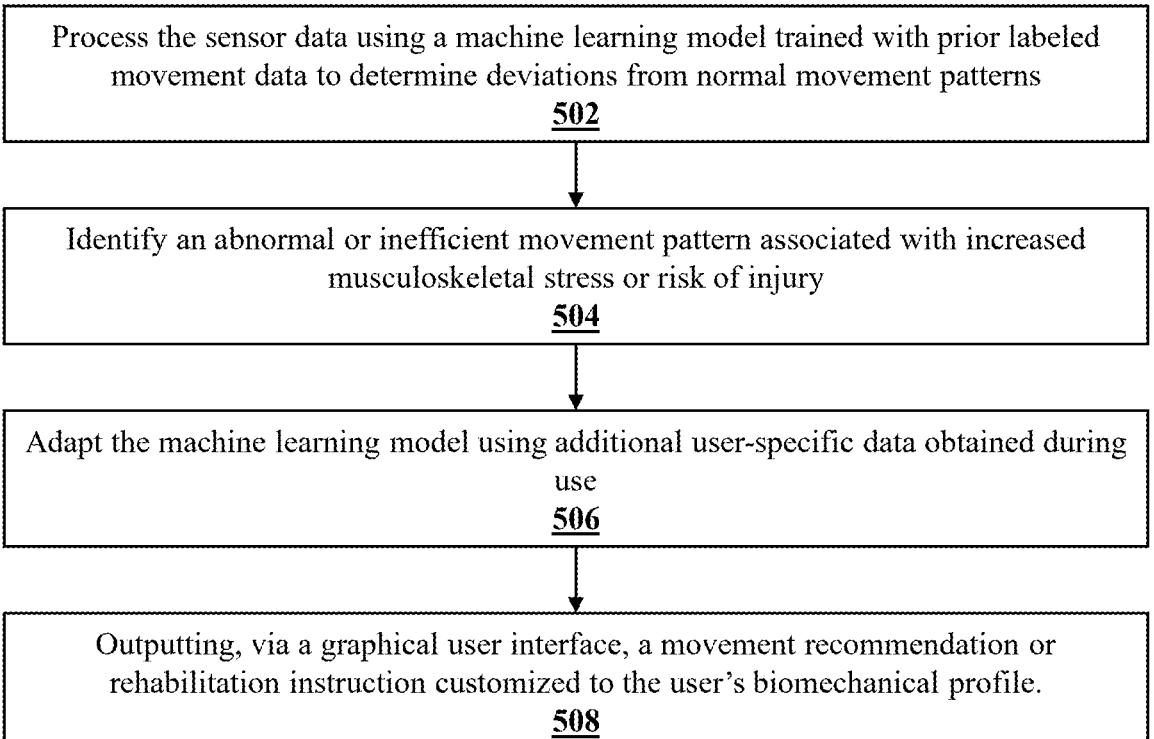

Process the sensor data using a machine learning model trained with prior labeled movement data to determine deviations from normal movement patterns
<u>502</u>

Identify an abnormal or inefficient movement pattern associated with increased musculoskeletal stress or risk of injury
<u>504</u>

Adapt the machine learning model using additional user-specific data obtained during use
<u>506</u>

Outputting, via a graphical user interface, a movement recommendation or rehabilitation instruction customized to the user's biomechanical profile.
<u>508</u>

FIG. 5

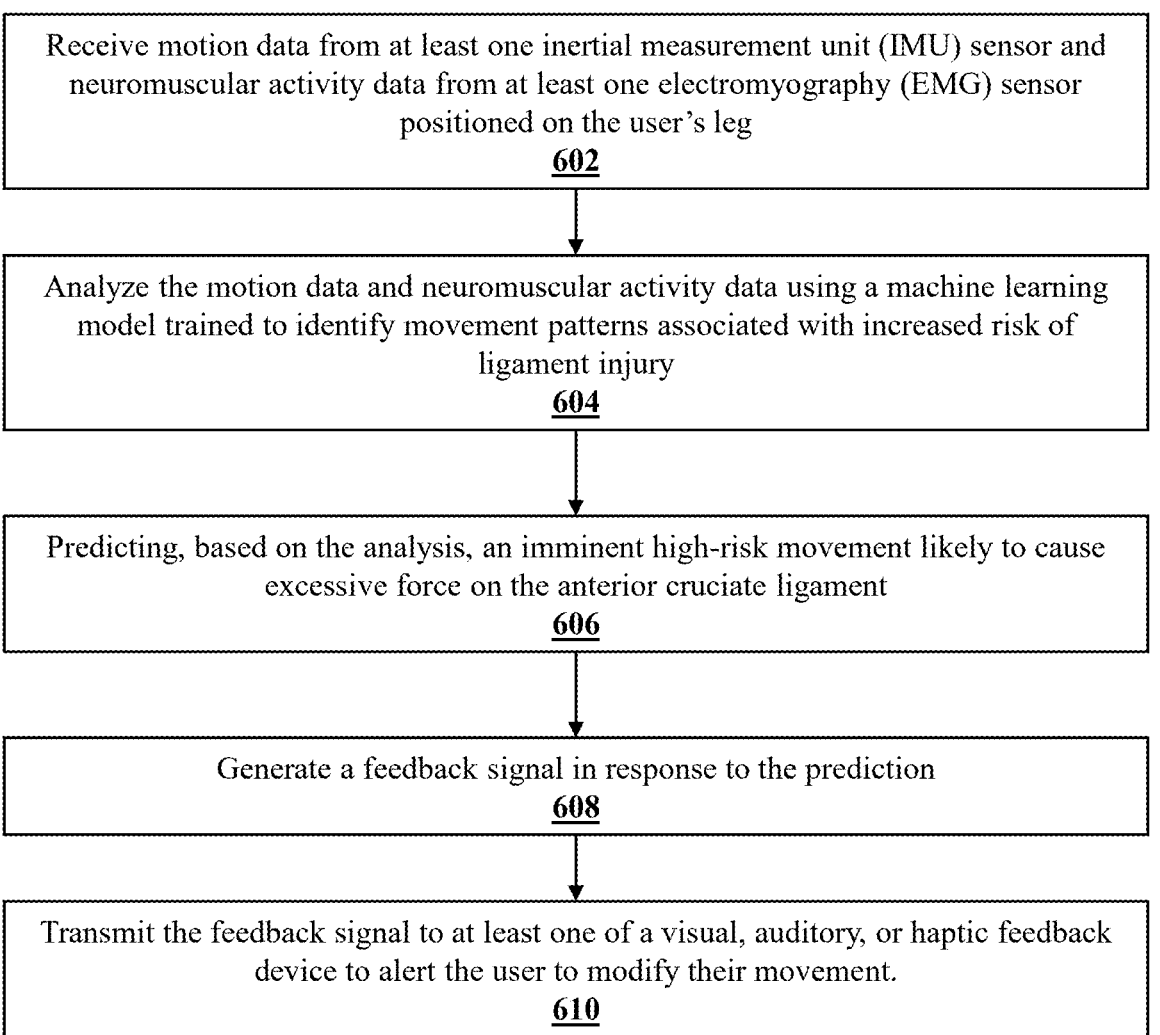

600

Receive motion data from at least one inertial measurement unit (IMU) sensor and neuromuscular activity data from at least one electromyography (EMG) sensor positioned on the user's leg
602

Analyze the motion data and neuromuscular activity data using a machine learning model trained to identify movement patterns associated with increased risk of ligament injury
604

Predicting, based on the analysis, an imminent high-risk movement likely to cause excessive force on the anterior cruciate ligament
606

Generate a feedback signal in response to the prediction
608

Transmit the feedback signal to at least one of a visual, auditory, or haptic feedback device to alert the user to modify their movement.
610

FIG. 6

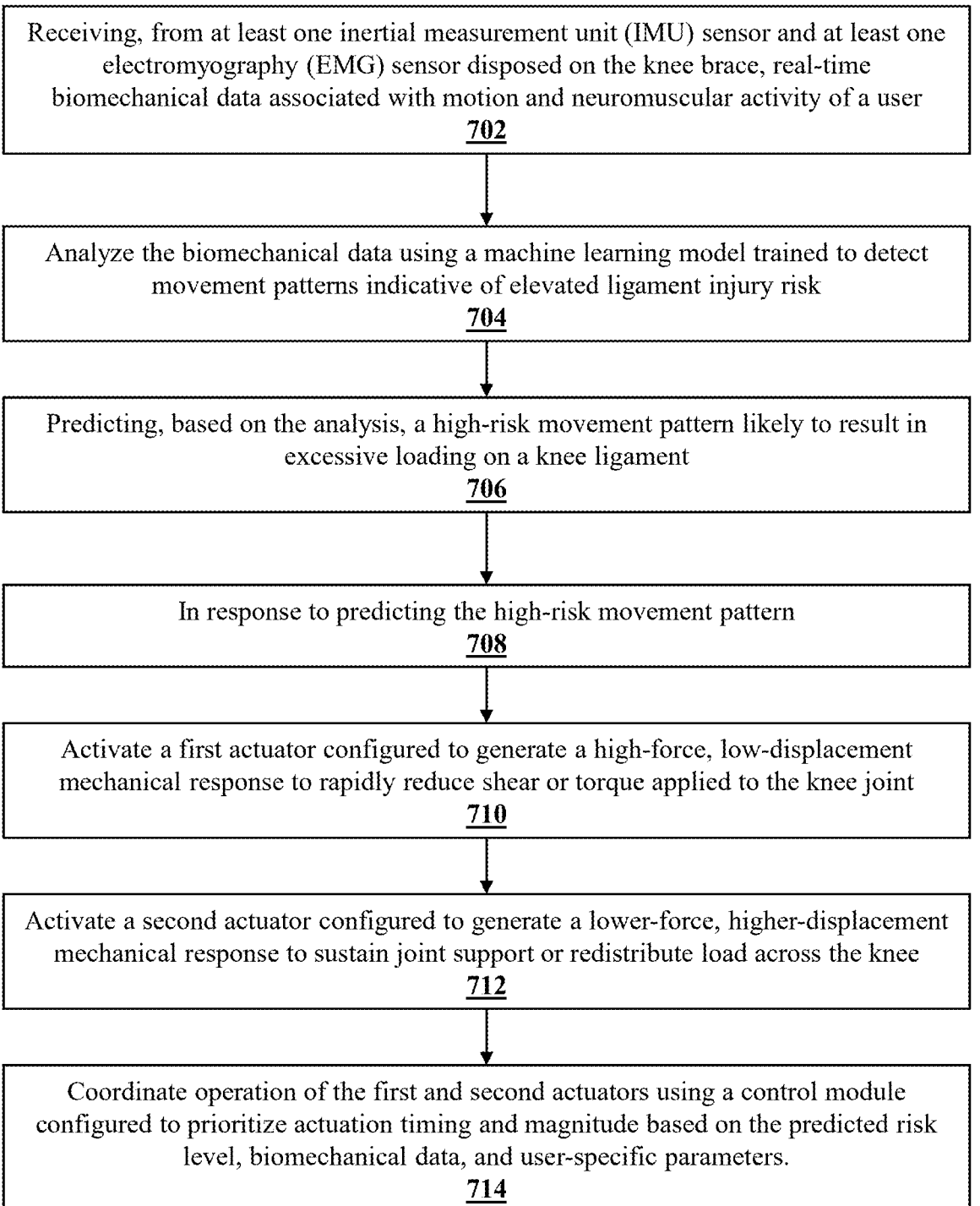

700

Receiving, from at least one inertial measurement unit (IMU) sensor and at least one electromyography (EMG) sensor disposed on the knee brace, real-time biomechanical data associated with motion and neuromuscular activity of a user
702

Analyze the biomechanical data using a machine learning model trained to detect movement patterns indicative of elevated ligament injury risk
704

Predicting, based on the analysis, a high-risk movement pattern likely to result in excessive loading on a knee ligament
706

In response to predicting the high-risk movement pattern
708

Activate a first actuator configured to generate a high-force, low-displacement mechanical response to rapidly reduce shear or torque applied to the knee joint
710

Activate a second actuator configured to generate a lower-force, higher-displacement mechanical response to sustain joint support or redistribute load across the knee
712

Coordinate operation of the first and second actuators using a control module configured to prioritize actuation timing and magnitude based on the predicted risk level, biomechanical data, and user-specific parameters.
714

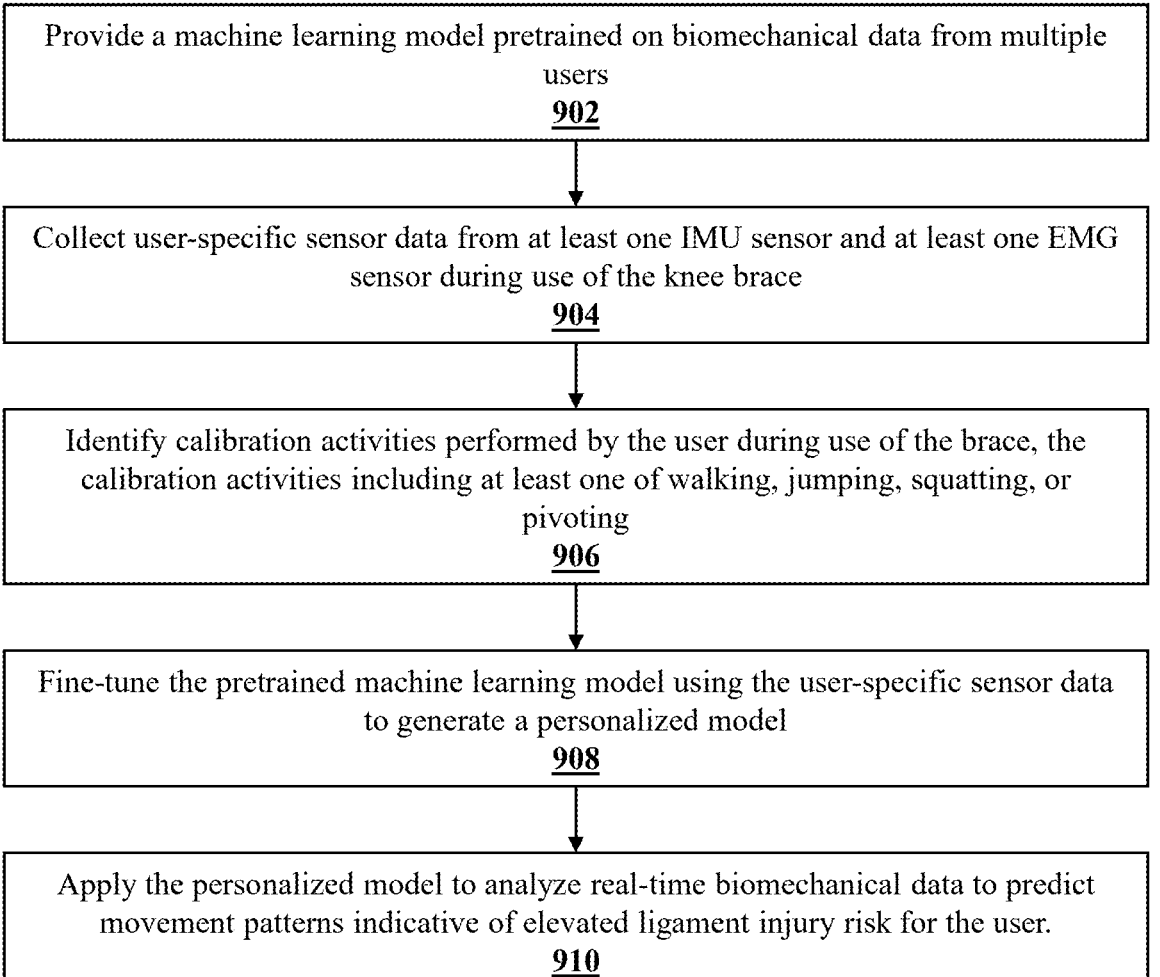

Provide a machine learning model pretrained on biomechanical data from multiple users
902

Collect user-specific sensor data from at least one IMU sensor and at least one EMG sensor during use of the knee brace
904

Identify calibration activities performed by the user during use of the brace, the calibration activities including at least one of walking, jumping, squatting, or pivoting
906

Fine-tune the pretrained machine learning model using the user-specific sensor data to generate a personalized model
908

Apply the personalized model to analyze real-time biomechanical data to predict movement patterns indicative of elevated ligament injury risk for the user.
910

FIG. 9

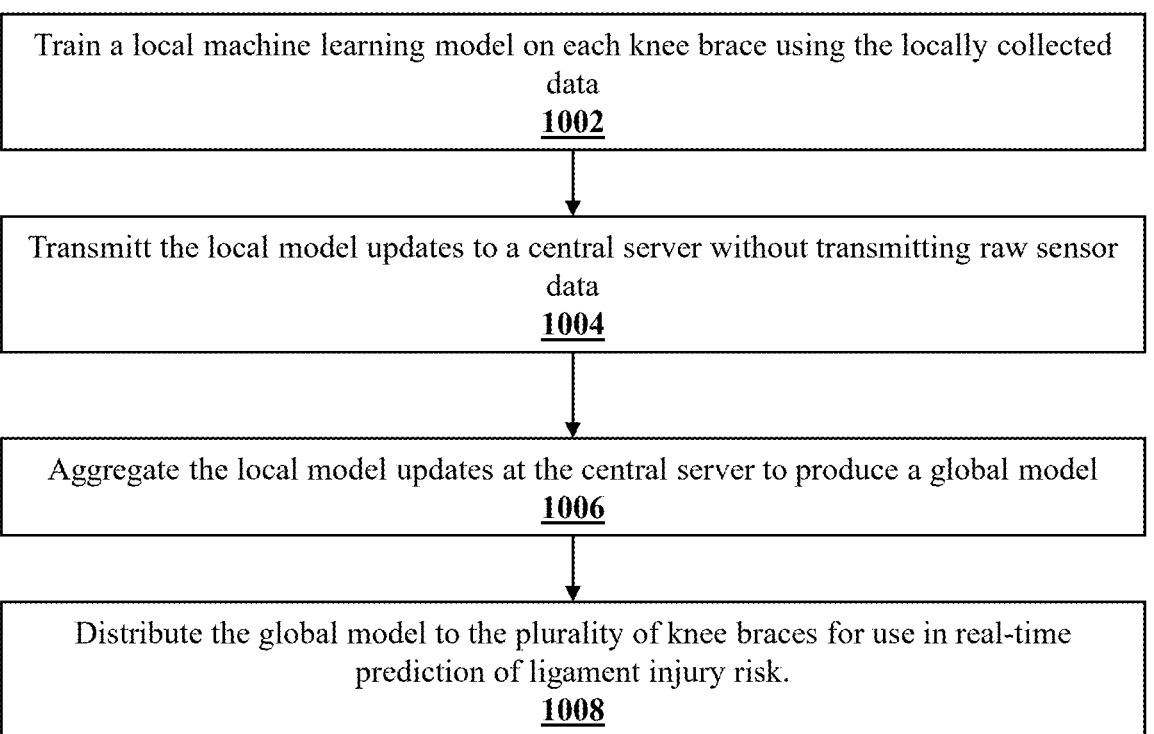

1000

Train a local machine learning model on each knee brace using the locally collected data
1002

Transmitt the local model updates to a central server without transmitting raw sensor data
1004

Aggregate the local model updates at the central server to produce a global model
1006

Distribute the global model to the plurality of knee braces for use in real-time prediction of ligament injury risk.
1008

FIG. 10

ANTERIOR CRUCIATE LIGAMENT PROTECTOR

CROSS REFERENCE TO RELATED APPLICATIONS

This application claims the benefit of U.S. provisional application Nos. 63/570,472 filed on Mar. 27, 2024, which is incorporated by reference as if fully set forth.

FIELD OF THE INVENTION

The present invention relates generally to wearable medical devices and orthopedic systems. More specifically, the invention pertains to sensor-integrated knee braces and associated methods for real-time biomechanical analysis, injury risk prediction, and active mechanical intervention using machine learning algorithms and responsive actuation systems.

BACKGROUND OF THE INVENTION

This patent discusses knee brace device that uses artificial force generation from actuators, machine learning, and sensors to protect the wearer against anterior cruciate ligament (ACL) and posterior cruciate ligament (PCL) injuries. The reported incidence rate of ACL injury in 2023 was 1 in 3500 people in the United States and 400,000 ACL reconstructions annually.[1] The societal cost ranges from $38K to $88K per patient in the United States.[2] The ACL is stretched or torn during sudden twisting motions, leading to higher likelihood of injury while dancing, playing sports, skiing, or serving in the military. The PCL is also subject to injury, usually caused by sudden, direct impacts, such as those in car accidents or football tackles.[3]

Existing knee braces are typically used after an injury occurs, and do not suffice for injury prevention. Currently, evidence that using existing knee braces when returning to sports post-injury decreases the rate of reinjury after ACL reconstruction. The rate of retear after ACL reconstruction is between 8 to 23% for athletes.[4] 63% of surgeons recommend using knee braces when returning to sports, but some studies found that patients wearing knee braces were more likely to see increased compression on the soft tissues of the limb, experience higher thigh atrophy, limited flexion range of motion, and altered muscle activation.[4,5] Active knee braces for gait and rehabilitation have been proposed and reviewed, but not for advanced injury prevention.[6]

The knee joint is complex, having 6 degrees of motion, encompassing 3 rotations and 3 translations. The primary knee rotational movement are flexions and extensions, determined by bending and straightening of the leg. The other 2 types of rotations include internal and external rotation of the tibia relative to the femur and varus and valgus angulation. The translational movements consist of anterior and posterior glide, medial and lateral shift, compression and distraction. The knee also bears weight, making it more prone to injury. It is stabilized by four major ligaments: the ACL prevents the tibia bone from moving too far forward, the PCL is situated behind the ACL and controls backward movement of the tibia, the medial collateral ligament (MCL) is on the inner side of the knee providing stability to the inner knee joint, and the lateral collateral ligament (LCL) provides stability to the outer knee. These ligaments are elastic bands of tissue connecting bones and overall provide stability. Anterior-posterior translation, defined as a measurement of how much the tibia moves relative to the femur, and internal-external rotations of the knee are important to its normal function.[7]

The ACL is subject to most injury out of the four ligaments, followed by the PCL. The ACL consists of type I (90%) and type III collagen. The average length of ACL ranges from 27 to 38 mm and the width from 10 to 12 mm. The cross-section area measures approximately 44 mm.[2] A healthy tendon stiffens in response to normal levels of forces applied to it. When the maximum load for an individual tendon is exceeded, the tendon may be strained and tear. The maximum load to failure for an intact ACL is 2160±157 N for a study of female, younger participants 22-35 years old. The linear stiffness was measured to be 242 (±28) N/mm.[8] With the tendon behaving like a spring, the amount of stretch before failure can be calculated along 1 linear axis, F=kx, where x is the stretch and k is the stiffness. With an increase in age, structural properties of the femur-ACL-tibia complex, represented by linear stiffness, ultimate load, and energy absorbed decrease with age.[8]

With an observable force and stiffness, a control system can be designed to regulate the forces to the knee. The challenge of estimating the forces to the knee is a statistically determinate problem, with a reduction of grouping muscles, which may have a wide set of feasible muscle force distributions, into external forces per functional unit. These external forces to the knee can be calculated based on force measurements from sensors, leading to a problem with 3 knowns and 3 unknowns for a 3-dimensional analysis. Based on these external forces of muscle groups, the internal forces acting on the knee joint, namely the components of the tibial-femoral contact force and quadriceps muscle force, can be estimated with an assumption of the external and internal forces acting in equilibrium.[7]

To implement control actions, actuators are typically used in systems requiring movement. An actuator is a device that converts signals into mechanical energy or action. The input signal can be an electric signal or force, which is considered a mechanical signal. Different types of actuators exist: electromagnetic motors, pneumatic actuators, hydraulic actuators, fluidic actuators, and piezoelectric actuators. Out of the existing types of actuators, piezoelectric actuators have larger output forces, quicker responses, and insensitivity to magnetic effects, making them ideal for applications requiring precision and accuracy.[9] Piezoelectric actuators can produce the forces needed for the knee brace. Harnessing actuators, including any type of high-force actuators in addition to piezoelectric actuators, the knee brace device enacts a response from an actuator when a sensor detects a torque or force greater than the ACL can withstand. It then actuates piezoelectric actuators to absorb the torque and output the energy in the form of mechanical energy to the surrounding air particles or activation of quadriceps and hamstrings, depending on quantity of the input force and torque. The device immediately disengages allowing the user to continue her or his activity without delay. The device would also provide continual feedback to the user and would warn them when they are approaching triggering limits. This would help mitigate behavior that would lead to injury, even when the device was not triggering.

To obtain measurements of neuromuscular activity and motion metrics, electromyography (EMG) and inertial measurement unit (IMU) sensors will be used in the knee brace device at hand. EMG sensors measure neuromuscular activity based on nerve stimulation of the muscles. Specifically, they measure electrical impulses generated by muscle contractions by detecting voltage changes at the skin's surface or within the muscle tissue. When a muscle contracts, it generates an electrical signal due to the depolarization and repolarization of muscle fibers. EMG sensors capture these signals and convert them into data that can be analyzed for muscle activation patterns, fatigue levels, and neuromuscular performance. These sensors have been used in analyze knee muscle patters and in prosthetic hands, but they have not been integrated in an advanced knee brace for injury preventation.[10,11]

The IMU measures linear acceleration through accelerometers, angular rate and quaternion, a measure of angular rotation, through gyroscopes. For heading reference, magnetometers are used. IMU systems have been validated to measure joint angles during range of motion studies of wrists after surgical treatment.[12] IMU data is also used in the aerospace industry for guiding spacecraft orientation, unmanned aerial vehicles, and in-flight monitoring. Other types of sensors that can be used in the device of invention include pressure sensors and goniometers.

For analysis of inertial measurement unit and electromyography data, machine learning is used for pattern recognition and prediction of potentially hazardous movements of device wearers. Machine learning (ML) enables computers to learn from data and make predictions or decisions without being explicitly programmed. ML algorithms analyze patterns in data, recognize relationships, and improve their performance over time through trained data. Machine learning models can be trained using different approaches, such as supervised learning, where the system learns from labeled examples; unsupervised learning, which identifies hidden patterns in unlabeled data; and reinforcement learning, where the model consists of an agent interacting with an environment, receiving feedback, and selecting control actions based on the feedback from a defined reward function. ML is widely used in applications such as speech recognition, image processing, recommendation systems, medical diagnostics, autonomous systems, and control systems. Within control systems. ML is widely used to analyze time series data and predicting future states of any dynamic system, eliminating the need for constant user input. Neural network based strategies employ recurrent Neural Network (RNN) and Long Short Term Memory (LSTM) for system identification and predictive control.[13] Just examining inertial measurement unit data, a bidirectional LSTM can predict when ballet dancers will do a pirouette with a 75% accuracy.[14]

Another mechanism incorporating actuation and force offloading includes artificial muscles. Recent on artificial muscle fiber structures examine mammalian-skeletal-muscle-inspired single fiber actuator allows integration into strong bundles and high-power soft robotics with light-driven remote control. This actuator utilizes a unique combination of materials and structural design to achieve enhanced mechanical strength and actuation performance. The study demonstrates that the integration of specific fillers within a tailored polymer matrix results in improved actuation strain, stress, and energy density.[15,16]

The Following References, Further Contextualize the Invention and are Integrated by Reference in their Entirety 1. Anterior Cruciate Ligament Knee Injury—StatPearls—NCBI Bookshelf. Accessed Feb. 21, 2025. https://www.ncbi.nlm.nih.gov/books/NBK499848/2.
2. III R C M, Lane Koenig and MSKTMD, Gallo P, Scott D J, Jr B R B, Kurt P. Spindler M. Societal and Economic Impact of Anterior Cruciate Ligament Tears. *J BONE Jt Surg Inc*. Published online 2013.
3. Ligament Injuries to the Knee|Johns Hopkins Medicine. Accessed Feb. 21, 2025. https://www.hopkinsmedicine.org/health/conditions-and-diseases/ligament-injuries-to-the-knee
4. Marois B, Tan X W, Pauyo T, Dodin P, Ballaz L, Nault M L. Can a Knee Brace Prevent ACL Reinjury: A Systematic Review. *Int J Environ Res Public Health*. 2021; 18 (14): 7611. doi: 10.3390/ijerph18147611
5. Effects of a Functional Knee Brace on Leg Muscle Function-Jorma R. Styf, Olof Lundin, David H. Gershuni, 1994. Accessed Feb. 21, 2025. https://journals.sagepub.com/doi/abs/10.1177/036354659402200615
6. Advances in active knee brace technology: A review of gait analysis, actuation, and control applications-ScienceDirect. Accessed Feb. 21, 2025. https://www.sciencedirect.com/science/article/pii/S2405844024020917
7. Mow V C, Huiskes R. *Basic Orthopaedic Biomechanics and Mechano-Biology*. 3rd ed. Lippincott Williams & Wilkins; 2005.
8. Woo S L Y, Hollis J M, Adams D J, Lyon R M, Takai S. Tensile properties of the human femur-anterior cruciate ligament-tibia complex: The effects of specimen age and orientation. *Am J Sports Med*. 1991; 19 (3): 217-225. doi: 10.1177/036354659101900303
9. Ma X, Liu J, Zhang S, Deng J, Liu Y. Recent trends in bionic stepping piezoelectric actuators for precision positioning: A review. *Sens Actuators Phys*. 2023; 364: 114830. doi: 10.1016/j.sna.2023.114830
10. Lee H, Lee S, Kim J, et al. Stretchable array electromyography sensor with graph neural network for static and dynamic gestures recognition system. *Npj Flex Electron*. 2023; 7 (1): 1-13. doi: 10.1038/s41528-023-00246-3
11. Parajuli N, Sreenivasan N, Bifulco P, et al. Real-Time EMG Based Pattern Recognition Control for Hand Prostheses: A Review on Existing Methods, Challenges and Future Implementation. *Sensors*. 2019; 19 (20): 4596. doi: 10.3390/s19204596
12. Movement Analysis with Inertial Measurement Unit Sensor After Surgical Treatment for Distal Radius Fractures—PMC. Accessed Feb. 21, 2025. https://pmc.ncbi.nlm.nih.gov/articles/PMC7247043/13.
13. Machine learning and its impact on control systems: A review-ScienceDirect. Accessed Feb. 24, 2025. https://www.sciencedirect.com/science/article/abs/pii/S2214785321013808
14. Paluszek M, Thomas S, Ham E. *Practical MATLAB Deep Learning: A Projects Based Approach*. Apress; 2023.
15. Human-muscle-inspired single fibre actuator with reversible percolation|Nature Nanotechnology. Accessed Feb. 24, 2025. https://www.nature.com/articles/s41565-022-01220-2
16. Biomimetic cell-actuated artificial muscle with nanofibrous bundles|Microsystems & Nanoengineering. Accessed Feb. 24, 2025. https://www.nature.com/articles/s41378-021-00280-z?from PaywallRec=false

SUMMARY OF THE INVENTION

Conventional knee braces are primarily passive devices that provide static support, compression, or post-injury stabilization. Such devices lack the ability to detect real-time biomechanical risk, adapt to dynamic user movements, or respond to imminent injury scenarios. Existing sensor-enabled systems are often limited to data logging or retrospective analysis, offering little to no capability for on-the-fly intervention. Furthermore, current machine learning implementations in wearable technology either require centralized data aggregation—raising privacy concerns—or fail to account for individual biomechanical variability.

The present invention addresses these and other technical problems by providing an intelligent, sensor-integrated knee brace system configured to predict and prevent ligament injuries, including anterior cruciate ligament (ACL) and posterior cruciate ligament (PCL) injuries. The system incorporates one or more inertial measurement units (IMUs) and electromyography (EMG) sensors to collect real-time biomechanical and neuromuscular data from the user during movement. A machine learning model, which may be trained using supervised, transfer, or federated learning techniques, analyzes the incoming sensor data to detect movement patterns associated with elevated injury risk.

Upon predicting a high-risk movement, the system may respond by issuing real-time feedback via visual, auditory, or haptic cues, or by activating one or more actuators. In certain embodiments, a hybrid actuation system is employed, wherein a high-force, low-displacement actuator (e.g., piezoelectric) provides rapid joint stabilization, and a low-force, high-displacement actuator (e.g., pneumatic) provides sustained offloading or movement correction. The brace may further adapt to an individual user's biomechanics through personalized calibration or fine-tuning of the machine learning model using locally collected sensor data. In yet another embodiment, the brace participates in a federated learning network, wherein encrypted model updates are shared across devices to continuously improve performance while preserving user privacy.

Through this architecture, the invention provides a comprehensive solution for real-time injury prevention, rehabilitation guidance, and long-term biomechanical optimization. The system achieves technical improvements in wearable sensing, embedded machine learning, and responsive actuation, thereby advancing the field of intelligent orthotics and sports medicine.

BRIEF DESCRIPTION OF THE DRAWINGS

FIG. 4 is a flowchart depicting a method for using sensor input to detect excessive joint force and apply corrective actuation in a knee brace system.

FIG. 5 is a flowchart illustrating a method for generating personalized biomechanical feedback using machine learning and a graphical user interface.

FIG. 6 is a flowchart showing a method for real-time prediction of ligament injury risk based on sensor data and trained machine learning models.

FIG. 7 is a flowchart illustrating a method for hybrid actuation using both high-force, low-displacement and low-force, high-displacement actuators in response to predicted risk.

FIG. 9 is a flowchart showing a method for user-specific personalization of a machine learning model using calibration activities and local fine-tuning.

FIG. 10 is a flowchart illustrating a federated learning process for training a global machine learning model using distributed updates from multiple knee brace devices.

DETAILED DESCRIPTION

Figure 1:
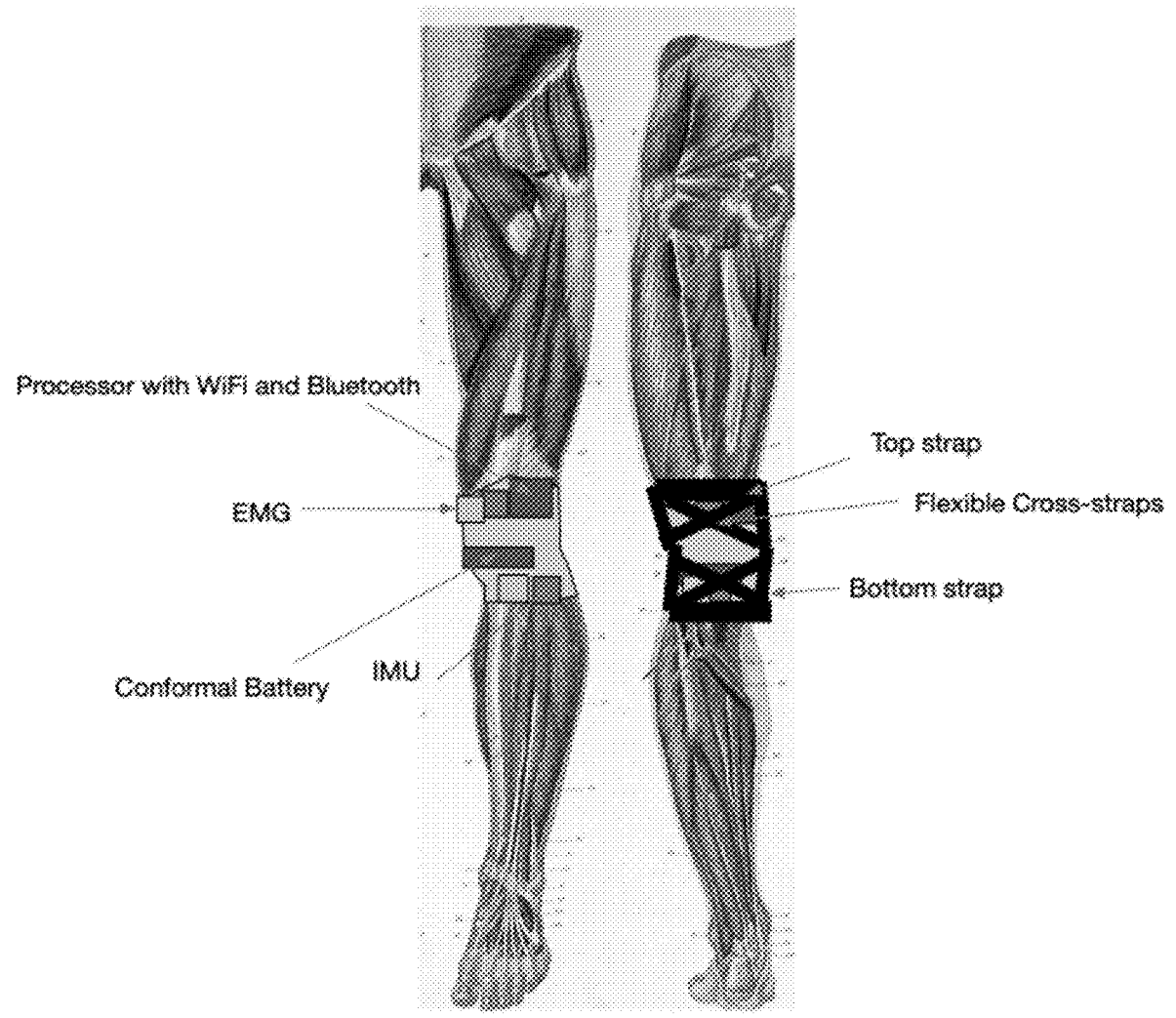
FIG. 1 is a schematic and structural illustration of an exemplary wearable knee brace system, including sensor, actuator, and control components.

Electromyography (EMG) is a method used to measure the electrical activity produced by skeletal muscles during contraction. EMG sensors may detect the electrical potentials generated by muscle fibers when they are activated by motor neurons. These signals can be used to assess muscle activation timing, intensity, fatigue, and coordination.

In some embodiments of the present invention, surface EMG (sEMG) sensors may be employed. Surface EMG sensors may be noninvasively placed on the skin overlying target muscles, such as the quadriceps, hamstrings, or gastrocnemius, to monitor neuromuscular activity associated with movement of the knee joint. These sensors may include one or more electrodes that detect voltage fluctuations caused by muscle depolarization and repolarization.

The raw EMG signal may be amplified and filtered to remove noise, motion artifacts, or powerline interference. The resulting signal may be processed in real time to extract features such as root mean square (RMS) amplitude, mean or median frequency, zero-crossing rate, or muscle activation onset time. These features may be used as input to a machine learning model or thresholding system to detect changes in muscle effort, asymmetry between muscle groups, or reduced neuromuscular control.

The integration of EMG sensors in the knee brace may enable the system to detect insufficient muscle engagement, muscular fatigue, or abnormal co-contraction patterns, all of which may contribute to elevated injury risk. For example, a low EMG signal from the hamstrings during a high-load landing maneuver may indicate that the anterior cruciate ligament (ACL) is absorbing excessive force, triggering a preventative response by the system.

EMG sensors may operate continuously or in conjunction with other sensors such as inertial measurement units (IMUs) to provide multimodal sensing of joint dynamics. The sensor hardware may be embedded within the brace, or affixed to the skin with adhesive pads or sleeves, and may communicate with the system's processor via wired or wireless connections.

A primary benefit of this system is injury prevention. By continuously analyzing biomechanical data, the machine learning model identifies movement patterns associated with musculoskeletal stress, fatigue, or potential injury risks. Upon detecting a high-risk movement, the system provides real-time alerts via haptic feedback, auditory warnings, or visual notifications, enabling users to make immediate adjustments. Athletes and physical therapists can leverage these insights to develop personalized training regimens emphasizing corrective exercises. Additionally, during rehabilitation, the system monitors progress and adapts activity recommendations to minimize the risk of re-injury.

Within the knee brace, the EMG and IMU sensors are strategically positioned on the quadriceps, hamstrings, and gastrocnemius to monitor muscle activity surrounding the knee joint. This allows the system to analyze stabilization patterns and detect imbalances that may predispose an individual to ACL injuries. Real-time feedback enables users to adjust their movement patterns, reducing injury risk and improving biomechanical efficiency.

The knee brace is particularly beneficial in rehabilitation settings, where patients recovering from orthopedic injuries require continuous monitoring of movement and muscle activation. The system provides real-time feedback to both the patient and their physical therapist, ensuring correct form and technique during rehabilitation exercises. By analyzing historical rehabilitation data, the machine learning model can predict potential setbacks and suggest alternative recovery strategies tailored to the user's biomechanics.

The knee brace is also applicable in medical diagnostics and telemedicine, allowing for remote monitoring of patients with neuromuscular disorders such as Parkinson's disease or multiple sclerosis. AI-driven analytics detect subtle changes in movement patterns, assisting healthcare professionals in tracking disease progression and making informed treatment decisions.

The combination of these datasets enables the detection of movement inefficiencies, identification of compensatory behaviors, and assessment of muscle fatigue. For example, if IMU data detects an abnormal gait pattern while EMG data reveals asymmetrical muscle activation, the system alerts users to correct their posture or modify their movement strategy. This is particularly beneficial in rehabilitation, where precise monitoring of muscle engagement and movement symmetry is critical for recovery.

The machine learning framework employs a hybrid modeling approach. CNNs process spatial data from IMU and EMG signals, while RNNs and LSTMs analyze temporal dependencies in movement patterns. Anomaly detection models, such as autoencoders and Gaussian mixture models, flag irregular muscle activity or high-risk movements. Transfer learning enables the model to adapt to new users with minimal retraining, and federated learning ensures privacy while allowing continuous improvement across decentralized devices. Reinforcement learning dynamically fine-tunes user feedback mechanisms, optimizing movement recommendations based on real-time biomechanical responses.

Once the model is sufficiently trained and calibrated, the system can operate without the need for an external registration camera, reducing system complexity and power consumption. This enhances portability, usability, and privacy, making the knee brace suitable for real-world applications in sports training, rehabilitation, and injury prevention.

Through continuous refinement, this intelligent knee brace ensures that users receive personalized, high-fidelity biomechanical insights, enabling optimized rehabilitation, enhanced athletic performance, and effective injury prevention strategies applicable to dancers, athletes, skiers, runners, and walkers.

The machine learning models used in the present knee brace system may be trained through a multi-phase process that includes initial offline pretraining, optional user-specific fine-tuning, and, in some embodiments, ongoing adaptation based on real-world usage data. These models may be implemented to analyze sensor input from inertial measurement units (IMUs), electromyography (EMG) sensors, and other biomechanical sensors to detect high-risk movement patterns or neuromuscular abnormalities.

In some embodiments, the training process may begin with a data collection phase involving a cohort of users performing various physical activities such as walking, running, jumping, pivoting, squatting, or cutting maneuvers. During these activities, time-series sensor data may be collected, including IMU-derived motion metrics such as linear acceleration, angular velocity, and quaternion-based orientation, as well as EMG-derived muscle activation signals from muscle groups including, but not limited to, the quadriceps, hamstrings, and gastrocnemius. The recorded data may be labeled manually or algorithmically to reflect different movement risk levels (e.g., "safe," "inefficient," or "high-risk") based on joint kinematics, biomechanical thresholds, or comparisons with gold-standard motion capture systems.

The training dataset may be used to supervise the development of one or more machine learning models. These models may include, for example, convolutional neural networks (CNNs) for spatial pattern extraction, recurrent neural networks (RNNs) or long short-term memory (LSTM) networks for time-series prediction, autoencoders for anomaly detection, or transformer models for sequence modeling. In some cases, reinforcement learning algorithms may be employed to optimize real-time actuation or feedback policies based on biomechanical state transitions.

Training may involve feeding labeled time-series sensor data into the model across sliding windows of fixed duration, such as 100 milliseconds to several seconds. The model may be trained to output classification probabilities (e.g., "at-risk" vs. "safe") or regression outputs such as estimated ACL load in Newtons. A loss function such as cross-entropy loss or mean squared error may be used, and optimization may be performed using stochastic gradient descent or its variants.

Once the base model is trained on population-level data, it may be adapted to individual users using transfer learning. For example, the model may be fine-tuned using a small set of calibration data collected during the user's initial use of the brace, such as walking or jumping trials. Fine-tuning may involve adjusting the model's weights or freezing certain layers to preserve generalized features while customizing others. This enables the model to account for user-specific movement characteristics, such as gait asymmetries or muscle recruitment patterns, which may not be captured in the original dataset.

In certain embodiments, the knee brace system may support ongoing model refinement through on-device learning or federated learning. In on-device learning, the system may continue to collect sensor data during normal use and retrain portions of the model periodically using privacy-preserving methods. In federated learning, multiple users' devices may compute local model updates based on private data and share only encrypted gradient updates or weight changes with a centralized server. This approach allows the model to improve over time across a distributed user base without exposing raw personal data.

The trained models may be evaluated for prediction accuracy, latency, robustness to sensor variability, and false-positive or false-negative rates. Performance thresholds may be set to optimize safety and usability depending on the intended context of use, such as injury prevention, rehabilitation, or performance optimization in athletic or dance training settings. The final deployed model may be compressed, quantized, or pruned to allow efficient real-time inference on low-power embedded processors integrated within the knee brace.

The anterior cruciate ligament (ACL)-protective knee brace described herein may be implemented in a variety of configurations, depending on the intended use case, user profile, and performance requirements. In general, the knee brace may comprise structural supports, embedded sensors, actuators, a power source, and one or more closed-loop user feedback mechanisms. The components and design features may be modular, customizable, or integrated into a unitary system. Several exemplary embodiments are described below, though the invention is not limited to these specific implementations.

In one embodiment, the knee brace may take the form of a lightweight, sleeve-style wrap constructed from neoprene, elastomeric knit, or other breathable composite fabric. This passive-style brace may include embedded surface electromyography (EMG) electrodes adhered to the interior surface of the sleeve, positioned over key muscle groups such as the quadriceps and hamstrings. Inertial measurement units (IMUs) may be sewn or laminated into the upper and lower sleeve portions to monitor relative motion of the femur and tibia. A compact microcontroller may be embedded near the lateral side of the knee, and a Bluetooth® or other low-energy wireless module may transmit sensor data to an external computing device such as a smartphone or smartwatch. This embodiment may function as a sensor-driven feedback tool, issuing real-time warnings to the user through auditory tones, haptic vibrations, or app-based notifications when unsafe joint motion is detected, such as anterior tibial translation during a pivot. The device may allow unrestricted joint movement and be particularly suited for training, early rehabilitation, or low-profile use in daily activities.

In another embodiment, the knee brace may incorporate rigid mechanical struts along the medial and lateral sides of the leg, forming a semi-rigid frame anchored by adjustable cuffs or pads around the thigh and shin. These struts may be connected via a pivoting hinge aligned with the anatomical axis of the knee. The brace may feature multiple tensioning straps spanning across the anterior and posterior knee, as well as diagonally arranged cross-straps. Piezoelectric, servo-electric, or pneumatic actuators may be operatively connected to these straps through a ratcheting, spool-based, or cable-pulley mechanism. In this embodiment, when the system detects high-risk joint motion—such as excessive internal rotation or valgus alignment in conjunction with low hamstring activation—the actuator system may engage to rapidly tighten specific straps. This tensioning action may apply counter-forces that redirect load away from the ACL. Once the risk subsides, the actuator may automatically relax the strap, restoring freedom of motion. This embodiment may be useful for sport-specific use or individuals at elevated risk of re-injury.

In a more structurally robust embodiment, the brace may be designed as an exoskeletal orthotic system comprising rigid composite thigh and shin segments joined by an articulating hinge. Load cells or torque sensors may be integrated into the hinge mechanism or cross-members of the frame to measure applied forces directly. Goniometers or flexible resistive sensors may be used to track angular displacement of the joint. A rechargeable battery and onboard processing unit may be housed in the posterior thigh component, with optional support for wireless charging. This brace may be capable of bearing higher loads and resisting extreme joint motions, making it well-suited for skiing, military training, or occupational use. It may also support high-fidelity biomechanical data collection for research or clinical diagnostics.

In another embodiment optimized for physical rehabilitation, the knee brace may be constructed to provide real-time visual, auditory, and digital feedback to support treatment goals. A mobile application or tablet-based interface may allow physical therapists to monitor patient progress, configure risk thresholds, and deliver movement guidance. The brace itself may incorporate a strip of color-coded LEDs positioned along its outer edge to indicate movement quality in real time, such as turning red for poor control or green for safe alignment. The system may track patient progress over time, detect compensatory movement patterns, and adjust recommendations accordingly. In this use case, actuation may be de-emphasized in favor of providing rich, user-specific analytics and feedback. The system may optionally support cloud connectivity, enabling remote review of patient data by clinicians or athletic trainers, and may include gamified exercise modes to promote patient adherence and motivation.

In yet another embodiment, the brace may incorporate soft robotic actuation components. These may include pneumatically inflated chambers or hydraulically filled channels embedded within a fabric sleeve or textile frame. The actuators may be positioned to mirror the alignment of key muscle groups and may activate to assist or resist movement in a biomimetic manner. For example, the brace may apply assistive force during knee extension or generate resistance during eccentric loading. This embodiment may enable fine-grained mechanical support while preserving comfort and flexibility. Actuation patterns may be dynamically controlled in response to sensor input, allowing the brace to adapt to varying biomechanical demands such as walking, stair-climbing, or balance recovery.

Across these embodiments, the brace may include a variety of power and control options. In some cases, a rechargeable lithium-ion battery may be embedded in the structural frame, while in others, flexible battery technologies or replaceable coin cells may be used for lightweight, low-power systems. The processing system may include a signal acquisition module, digital signal processor, real-time clock, and secure memory to store calibration parameters, sensor logs, or machine learning weights. Models may be executed locally or offloaded to a mobile device depending on computational demands and latency constraints. In embodiments incorporating actuation, safety protocols may be implemented to prevent overcorrection, excessive force application, or actuation in unintended situations.

The brace may be worn directly against the skin or over a thin garment and may include a removable comfort sleeve or integrated cooling layer. It may be made available in multiple sizes or in a customizable form factor using 3D-printing or molding techniques. In certain cases, the brace may be paired with other wearable systems—such as smart insoles, hip-worn accelerometers, or inertial capture suits—for enhanced situational awareness or full-body biomechanical monitoring.

Through these varied implementations, the knee brace system may serve a broad spectrum of users—from professional athletes seeking to prevent injury, to patients undergoing rehabilitation, to clinicians seeking high-fidelity diagnostic data-by combining mechanical support, real-time sensing, and intelligent control in a single wearable platform.

In one embodiment, the knee brace system may implement a hybrid actuation architecture that combines multiple actuator types to optimize performance across a range of biomechanical scenarios. This hybrid system may leverage the complementary characteristics of high-force, low-displacement actuators (e.g., piezoelectric) and low-force, high-displacement actuators (e.g., pneumatic or hydraulic), thereby enabling both rapid protective intervention and longer-duration support or rehabilitation functions.

The system may include at least one primary actuator, such as a piezoelectric actuator, positioned to apply rapid, short-range corrective forces in response to high-risk motion events. These events may be detected using the system's IMU and EMG sensors and confirmed via the real-time injury prediction module. Upon detecting an imminent injury condition—such as sudden anterior tibial translation or internal rotation exceeding threshold levels—the primary actuator may engage within milliseconds to pre-tension cross-straps or stabilize the hinge assembly. The goal of this actuation is to counteract shear forces acting on the anterior cruciate ligament (ACL) before tissue strain exceeds the failure threshold.

Concurrently or subsequently, the system may activate a secondary actuator, such as a pneumatic or servo-electric actuator, capable of applying sustained tension or displacement to redistribute force loads and assist in joint stabilization. For example, a pneumatic bladder embedded within the lateral support structure may gradually inflate to reinforce the knee's mechanical alignment or relieve muscle groups under high strain. This secondary actuator may be slower in response but capable of higher displacement, making it suitable for tasks such as correcting valgus collapse, supporting eccentric movements during rehabilitation, or maintaining a desired joint position during post-fatigue stabilization.

The hybrid actuation logic may be coordinated by a centralized control module that prioritizes actuator engagement based on real-time biomechanical data, machine learning model outputs, and pre-configured user profiles. In some embodiments, a tiered response system may be employed. For low-risk deviations, the system may deliver haptic feedback only; for moderate risk, it may engage the secondary actuator for mechanical guidance; and for high-risk events, it may activate both actuators in sequence or simultaneously to execute a protective response.

This hybrid system may also adapt its actuation strategy over time. For example, during early rehabilitation, the system may favor longer-duration, low-force pneumatic actuation to assist weakened musculature. As the user progresses, the system may shift toward rapid, high-force interventions to enable return-to-play scenarios while minimizing re-injury risk.

In some cases, the hybrid system may incorporate redundant actuation to ensure fail-safe performance. For instance, if the primary piezoelectric actuator fails to engage or cannot achieve the required force output, the secondary actuator may automatically compensate by increasing pressure or displacement to maintain joint protection.

By combining actuation types with complementary mechanical profiles, the hybrid system maximizes the protective, assistive, and rehabilitative capabilities of the knee brace. This embodiment allows the device to operate across a wider range of activity intensities, user conditions, and clinical requirements, delivering biomechanically appropriate support with both precision and adaptability.

In some embodiments, the knee brace system may incorporate a federated learning framework designed to enable distributed training of machine learning models across a plurality of wearable devices, without transmitting raw biomechanical sensor data to a centralized server. This framework facilitates collaborative model improvement while preserving user privacy, reducing network bandwidth consumption, and supporting continuous system adaptation across diverse users and activities.

In some embodiments, one or more actuators may be integrated into the knee brace system to apply dynamic mechanical responses in real time based on predicted ligament injury risk. The actuators may be mechanically and electrically coupled to structural components of the brace, such as straps, hinge assemblies, or embedded artificial muscle channels, and may be controlled by a processing unit executing injury prediction and control algorithms.

The actuator subsystem may be implemented using various technologies depending on the desired force, displacement, response time, and energy efficiency characteristics. In one embodiment, a piezoelectric actuator may be embedded within the brace's lateral support strut or hinge housing and configured to rapidly generate tensile force when electrically stimulated. The piezoelectric actuator may engage a mechanical linkage, such as a ratchet, cable spool, or micro-servo assembly, to tension a strap positioned across the anterior or posterior region of the knee joint. This high-speed actuation may be triggered in less than 50 milliseconds following a high-risk movement prediction, serving to oppose anterior tibial translation or internal rotation.

In another embodiment, a pneumatic actuator may be embedded within a soft bladder channel positioned along the medial or lateral sides of the knee brace. Upon detection of an elevated injury risk condition, a miniature air pump or compressed $CO_2$ cartridge may inflate the bladder, causing it to stiffen and apply a directional force to realign the joint or increase resistance to valgus collapse. The pneumatic actuator may be held in its active state for a predefined duration or until biomechanical stability is restored, after which it may be deflated passively or through a vent valve.

In yet another embodiment, the actuator may comprise a shape-memory alloy (SMA) wire integrated within a flexible tendon or strap that runs diagonally across the knee joint. When heated by an applied current, the SMA wire contracts, pulling on the strap to tighten the brace and redistribute load. SMA actuation may be slower than piezoelectric or pneumatic systems but may be used in applications where sustained joint support or gradual alignment correction is desirable.

The actuators may be embedded within a rigid exoskeletal brace frame, sewn into textile channels in a flexible fabric brace, or mounted to modular anchor points for ease of maintenance or customization. In each case, the actuator may be operably coupled to a control unit, which receives signals from a real-time machine learning model running on an embedded processor. The control unit may convert model output probabilities into actuator commands using a predefined response policy or rule-based actuation logic.

Power for the actuator system may be supplied by a rechargeable lithium-ion battery integrated into the thigh or calf region of the brace. In some implementations, actuator drivers (e.g., MOSFETs, amplifiers, or valve controllers) may be co-located with the battery and processor in a compact electronics module. Safety features, such as current limiters, mechanical stops, and automatic disengagement thresholds, may be incorporated to prevent overcorrection, excessive force application, or actuation during low-risk movement.

In hybrid actuation embodiments, multiple actuators of different types may be coordinated to engage in a staged or prioritized sequence. For example, a piezoelectric actuator may engage immediately to apply a short-duration counter-force, followed by a pneumatic actuator inflating to stabilize the joint over a longer interval. A central coordination algorithm may resolve conflicts, manage timing, and adapt actuator behavior to user-specific profiles or movement contexts.

This actuator integration architecture allows the knee brace system to provide responsive, biomechanically informed intervention in real time, enabling both preventative and rehabilitative support tailored to the user's dynamic physical state.

Each knee brace may be equipped with a local model training system. This training functionality may be embedded directly in the processor of the brace or may be executed on a paired computing device, such as a smartphone, tablet, or smartwatch. The device maintains a copy of a shared machine learning model architecture, which may include convolutional neural networks (CNNs), recurrent neural networks (RNNs), or transformer-based models. The training system accesses sensor data recorded locally by the brace, including time-series inputs from one or more inertial measurement units (IMUs) and electromyography (EMG) sensors. These inputs reflect user-specific joint motion and neuromuscular activity patterns during activities such as walking, squatting, pivoting, or jumping. The training engine may perform optimization using stochastic gradient descent (SGD), policy-gradient reinforcement learning, the Adam optimizer, or privacy-enhanced methods such as differentially private SGD, thereby updating model weights based on local data. In some embodiments, the device may also include a validation module to ensure that the updated model maintains or improves accuracy on user-specific inputs before it is shared with the network.

Once local training is complete, the updated model parameters are prepared for secure transmission to a central aggregation server. To preserve privacy, the device may transmit only the learned model updates-such as gradient vectors or revised weight matrices-without sharing the underlying sensor data. The transmission process may include data packaging, encryption, or anonymization techniques to ensure that no personal or reconstructable information is exposed. Secure communication protocols such as HTTPS, TLS, or federated learning-specific frameworks leveraging secure multiparty computation or homomorphic encryption may be used to protect the transmission.

The central aggregation server receives model updates from a distributed network of devices. It includes a collector module for gathering incoming model parameters and an aggregation engine that combines them into a global model using federated averaging or another weighted update scheme. The aggregation process may take into account factors such as local dataset size, model performance, or temporal freshness of the update. In some embodiments, the server may implement anomaly detection algorithms to identify and exclude faulty or adversarial updates that could negatively affect model integrity. The result of this aggregation is a refined global model that reflects biomechanical learning across a wide range of users, activities, and environments, while preserving the confidentiality of each user's raw data.

Following aggregation, the global model is redistributed to the network of knee brace devices. A distribution service sends the updated model to each device through secure channels, optionally performing device compatibility checks to ensure the receiving hardware and software can support the model. Model deployment may be scheduled during low-usage periods or synchronized with firmware updates to minimize interference with real-time injury detection tasks. Once received, the global model may replace the previous model or be merged with a locally fine-tuned version using interpolation, ensemble learning, or additional training.

The federated learning process is coordinated by a central controller responsible for orchestrating each phase of the training cycle. The coordinator may determine when to initiate new training rounds based on fixed intervals, usage thresholds, or the number of active participants. It may also manage regulatory compliance, user opt-in preferences, and secure audit logging for system performance monitoring and verification. The system may further track the evolution of the global model over time, maintaining version control and rollback capabilities in the event of instability or model degradation.

Through this federated learning architecture, the knee brace system is able to continuously improve its machine learning capabilities across a diverse user base without ever collecting or exposing individual sensor data. The result is a robust, privacy-preserving predictive platform capable of identifying high-risk movement patterns and delivering biomechanically adaptive support with increasing accuracy over time.

FIG. 1 illustrates an exemplary embodiment of a knee brace system constructed in accordance with the present invention. The figure includes both a schematic view of internal components and a structural depiction of the brace in its worn configuration.

In the schematic on the left side of FIG. 1, the internal sensor and control components are shown integrated within the structure of the knee brace. One or more inertial measurement unit (IMU) sensors may be embedded within the upper and lower portions of the brace to detect motion, acceleration, angular velocity, and orientation of the femur and tibia. These sensors may be positioned to capture relative motion across the knee joint during dynamic activities such as jumping, pivoting, or sudden deceleration.

Electromyography (EMG) sensors may be included on the interior surface of the brace or embedded into an inner sleeve or patch that contacts the skin. These sensors may be placed over key muscle groups, such as the quadriceps, hamstrings, and gastrocnemius, to monitor electrical activity associated with muscular contractions. Data from the IMU and EMG sensors may be routed to a central processing unit housed within a rigid or semi-rigid casing positioned laterally on the brace or integrated into a thigh or calf segment.

Also shown is an actuator system configured to apply mechanical forces in response to injury risk detection. The actuator may include piezoelectric, servo-electric, pneumatic, or textile-based mechanisms that interact with strap elements of the brace. A motor or tensioning assembly may be configured to pre-tension or release one or more straps spanning across the front, back, or sides of the knee in order to counteract detected forces and reduce strain on the anterior cruciate ligament (ACL). In some embodiments, artificial muscles or contractile elements may replace or augment mechanical actuators.

On the right side of FIG. 1, a view of the exterior configuration of the brace is shown. The brace may be worn directly over the knee and secured in place using top and bottom circumferential straps. Cross-straps may extend diagonally across the knee joint to improve stability and provide surfaces for force redirection when actuated. The straps may be elastic, inelastic, or include regions of variable stiffness. The central portion of the brace may include a flexible joint or hinge mechanism allowing for natural flexion and extension while controlling rotational and translational movements. A soft sleeve or fabric wrap may surround the brace to improve comfort and conceal the underlying hardware.

The illustrated configuration is one of several possible implementations and is intended to show the relationship between structural elements and internal components. Additional sensors, feedback mechanisms, or therapeutic modules may be included depending on user needs, rehabilitation phase, or activity intensity.

Figure 2:
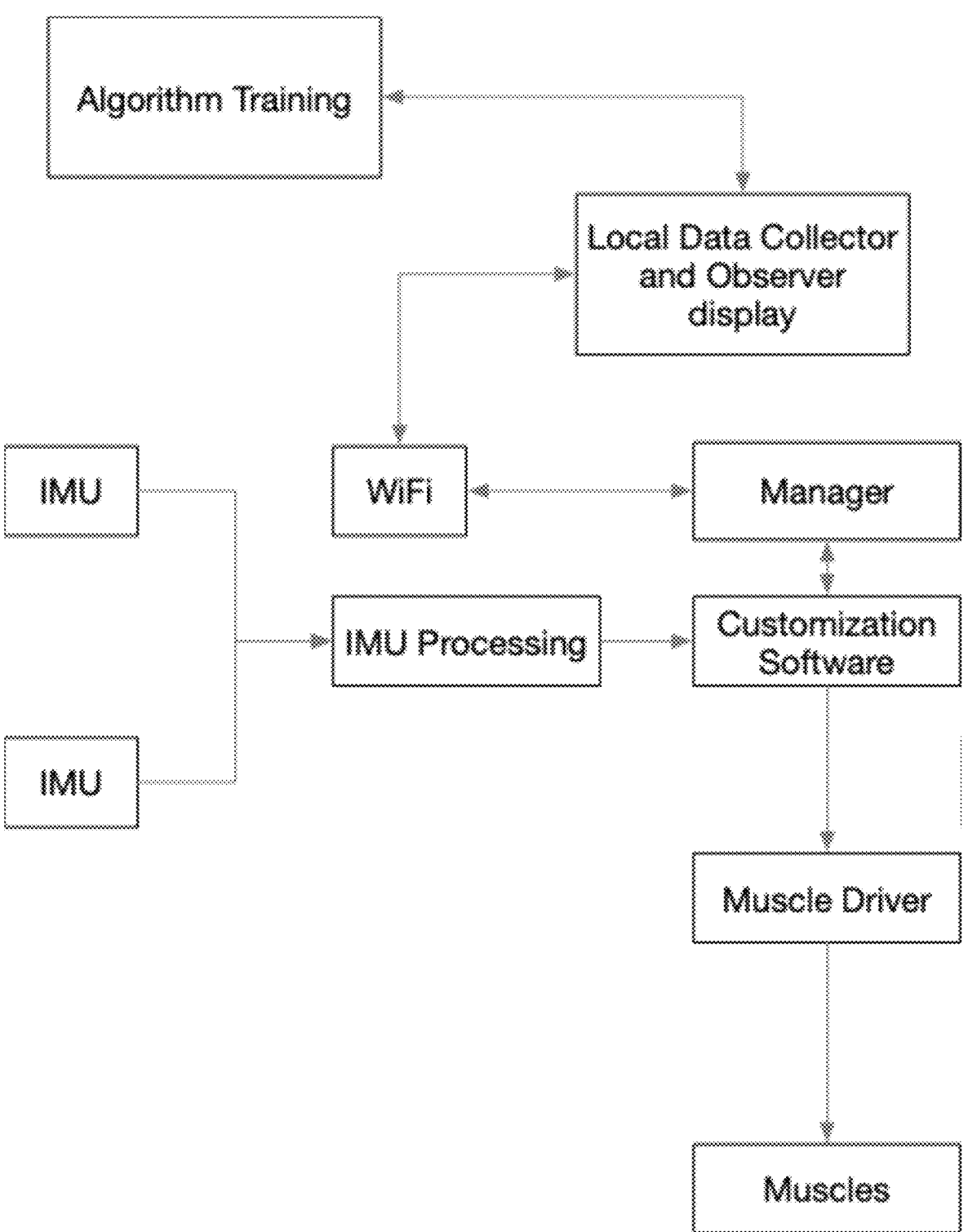
FIG. 2 is a block diagram illustrating a software architecture for real-time injury risk prediction and biomechanical feedback using sensor data and machine learning.

FIG. 2 illustrates an exemplary software architecture for a smart knee brace system configured to predict injury risk and provide real-time biomechanical feedback to the user. The architecture shown may be implemented across one or more hardware platforms, including embedded processors within the knee brace, a companion mobile device, and optionally a cloud-based analytics system.

The software stack may begin with a sensor acquisition layer, which interfaces with the inertial measurement unit (IMU) and electromyography (EMG) sensors integrated into the brace. This layer may handle sampling, analog-to-digital conversion, and preprocessing of raw sensor signals. Signal conditioning processes may include filtering, normalization, and artifact removal, such as band-pass filtering to isolate muscle activation frequencies in EMG data or smoothing algorithms to reduce IMU noise.

Processed sensor data may then be passed to a feature extraction module, which derives relevant biomechanical and neuromuscular features. For IMU data, extracted features may include joint angle estimates, angular velocity, linear acceleration, quaternion rotation, or computed measures such as jerk or gait cycle phase. For EMG data, features may include root mean square (RMS) amplitude, signal variance, activation timing, and inter-muscle coordination patterns.

A machine learning model module may receive the extracted features and perform predictive inference. This module may run a neural network architecture-such as a convolutional neural network (CNN), recurrent neural network (RNN), or long short-term memory (LSTM) network-trained to classify movements as low-, medium-, or high-risk, or to estimate joint loading values. The model may also implement anomaly detection algorithms or reinforcement learning policies that evolve over time. In some embodiments, the model may be trained offline and executed locally, while in other embodiments, training and inference may be distributed across connected devices or performed in the cloud.

Based on the model output, a decision logic layer may determine whether a control or feedback response is necessary. If the predicted movement exceeds an injury risk threshold or exhibits poor biomechanical form, this module may trigger downstream actions. These actions may include generating a control signal for actuation, initiating a feedback event, or logging data for further review.

The feedback layer may control one or more output modalities, such as haptic motors embedded in the brace, auditory cues from a connected device, or visual feedback displayed on a user interface. In some embodiments, a graphical user interface (GUI) may display live sensor streams, risk scores, suggested corrections, or rehabilitation progress. The GUI may be hosted on a mobile application, tablet, smartwatch, or desktop system, and may allow both user and clinician interaction.

Optionally, a data storage and analytics layer may archive sensor streams, predictions, and user responses over time. This data may be used to personalize model predictions, adapt feedback thresholds, or support remote clinical review. The system may also support cloud synchronization, secure data transmission, and user privacy protocols.

The software architecture depicted in FIG. 2 enables seamless integration between hardware sensing, intelligent prediction, and real-time feedback or actuation. The modular structure allows the system to be tailored for real-time prevention, post-injury rehabilitation, long-term monitoring, or athletic performance optimization.

Figure 3:
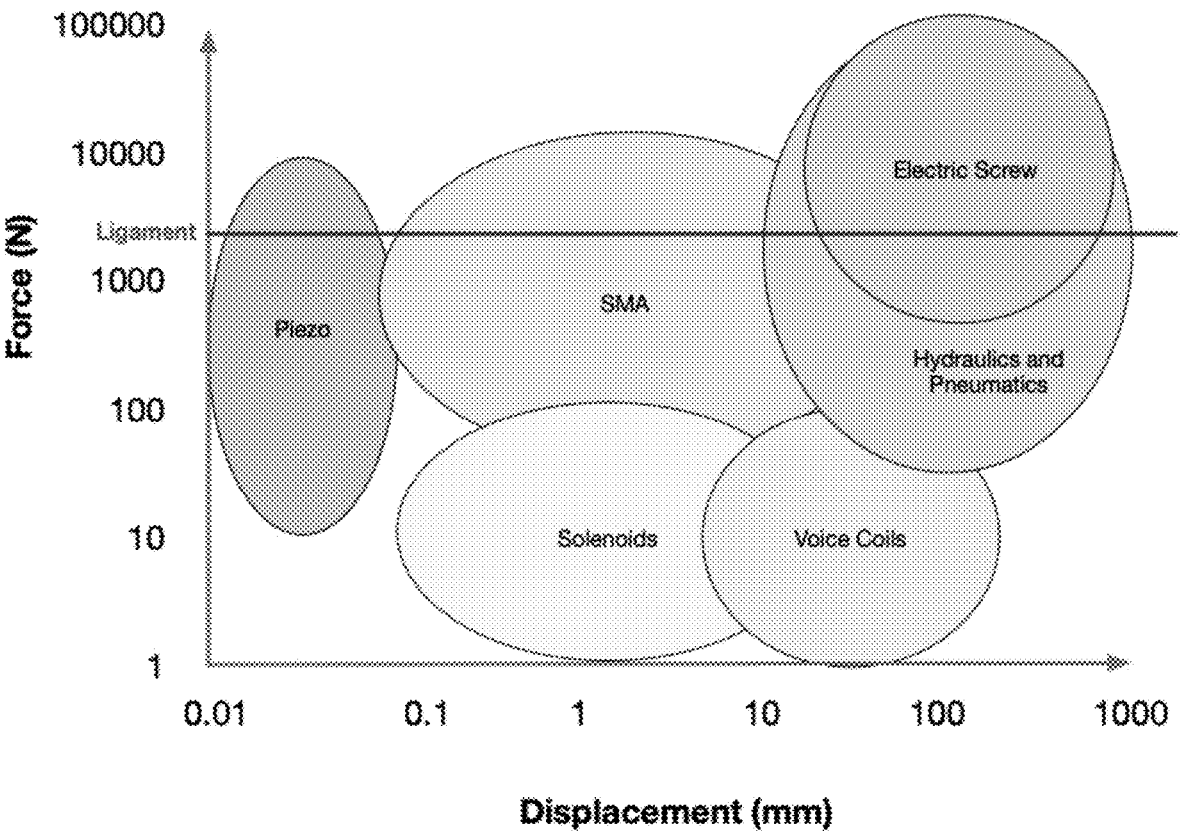
FIG. 3 is a graph comparing force and displacement characteristics for various types of actuators, illustrating trade-offs in actuator selection.

FIG. 3 illustrates a graph comparing various types of actuators based on their output force and displacement characteristics. The graph provides a visual reference for selecting an actuator suitable for the specific performance requirements of the knee brace system, particularly in the context of mitigating high-force events that may lead to anterior cruciate ligament (ACL) or posterior cruciate ligament (PCL) injury.

The x-axis of the graph represents displacement, while the y-axis represents force output. Multiple actuator types are plotted on the graph, each characterized by a curve or data point indicative of its performance envelope. These actuator types may include, for example, piezoelectric actuators, pneumatic actuators, hydraulic actuators, electromagnetic motors, and shape-memory alloy (SMA) actuators.

As shown, piezoelectric actuators are capable of generating high force over relatively small displacements. This makes them particularly advantageous for fast, precise actuation tasks such as rapidly pre-tensioning a strap or stiffening a support structure during a high-risk knee movement. In contrast, pneumatic and hydraulic actuators exhibit larger displacements and are better suited for applications requiring broader mechanical deformation or assistive motion over a longer stroke.

Electromagnetic actuators may offer moderate force and displacement performance, while SMA actuators may provide biologically inspired actuation at lower power levels but with slower response times.

The force-displacement mapping in FIG. 3 supports the selection and integration of actuator technologies based on the required intervention response of the knee brace. For instance, rapid force redirection or absorption during an impending ACL-straining movement may necessitate actuators that deliver high force with millisecond response latency. Alternatively, rehabilitation or fatigue-mitigation applications may benefit from actuators capable of producing controlled, gradual movement over a larger displacement range.

In some embodiments, hybrid actuator systems may be employed to balance force output, displacement, energy efficiency, and response time. The knee brace system may dynamically engage one or more actuator types depending on biomechanical sensor input, user profile, or predicted injury risk.

This graph provides engineering guidance for actuator selection and illustrates the design trade-offs between different actuation mechanisms in the context of wearable biomechanical protection and support.

FIG. 4 illustrates a method 400 that may be used by a knee brace system to detect biomechanical risk conditions and actively offload force from the knee joint using actuator-driven mechanisms. The method may be performed using a combination of IMU and EMG sensors, signal processing components, and a control system operatively coupled to one or more actuators integrated within the brace.

In step 402, the system may detect relative motion between a femoral attachment point and a tibial attachment point using at least one inertial measurement unit (IMU) sensor. The IMU sensor may comprise one or more accelerometers, gyroscopes, or magnetometers configured to measure relative angular displacement, acceleration, or orientation of the upper and lower brace components. This motion may correspond to translational or rotational movement of the knee joint during physical activity such as running, jumping, or sudden directional changes. The IMU data may be continuously sampled at high frequency (e.g., 100-1000 Hz) and optionally filtered to reduce signal noise.

In step 404, the system may detect muscle activation levels using at least one electromyography (EMG) sensor. The EMG sensor may be positioned on the user's quadriceps, hamstrings, or gastrocnemius muscles to monitor electrical activity associated with voluntary or reflexive muscle contractions. The EMG signal may be processed to extract features such as root mean square (RMS) voltage, signal amplitude, frequency content, or fatigue indices. These features may indicate muscle readiness, fatigue, or lack of engagement during key movement phases.

In step 406, the detected motion and muscle activation levels may be compared to one or more predetermined thresholds that are indicative of excessive force or torque on the anterior cruciate ligament (ACL). These thresholds may be static (based on general biomechanical studies) or adaptive (based on individual user calibration). For example, if the system detects a rapid anterior translation of the tibia relative to the femur, accompanied by insufficient hamstring activation, it may infer that the ACL is experiencing elevated tensile loading.

In step 408, if the comparison reveals that a measured value exceeds the injury risk threshold, the system may generate a control signal. This signal may be encoded in real time and transmitted to an onboard or external actuation controller. The control logic may include a decision-making module that prioritizes response speed and safety, optionally integrating additional context such as the user's activity state or history of joint instability.

In step 410, the control signal may be used to activate one or more actuators mechanically coupled to the knee brace. The actuators may apply targeted tension to one or more straps, belts, or artificial muscles embedded in or around the brace. In one embodiment, piezoelectric or pneumatic actuators may pre-tension the cross-straps or support structures in a direction that counteracts the detected force vector, thereby redistributing joint load to adjacent muscle groups or structural supports. In another embodiment, the actuator response may simulate the effect of muscular co-contraction by stiffening the brace at the moment of high-risk movement. The force may be offloaded away from the knee joint and dissipated mechanically, thermally, or through auxiliary muscle recruitment.

The actuation system may be configured to reset automatically once the high-risk condition subsides, returning the brace to a neutral or passive state. The actuation profile (e.g., tension level, duration, timing) may be adjusted based on ongoing sensor feedback, user-specific parameters, or machine learning-based optimization routines.

This method may operate as a standalone preventative control loop or in conjunction with the real-time prediction and feedback systems described in other embodiments. Together, these systems may enable both predictive and reactive ACL injury prevention in dynamic, real-world environments.

FIG. 5 illustrates a method 500 that may be implemented in a smart knee brace system to provide personalized movement recommendations and rehabilitation instructions through adaptive machine learning and graphical user interface feedback. This method may enhance injury prevention and post-injury recovery by enabling dynamic, data-driven support tailored to an individual user's biomechanics.

In step 502, the system may process real-time sensor data using a machine learning model trained on previously labeled movement datasets. The sensor data may be collected from inertial measurement units (IMUs), electromyography (EMG) sensors, or other biomechanical monitoring components integrated into the knee brace. The prior datasets may include motion capture or wearable sensor recordings of athletic, clinical, or daily movement patterns, labeled by physical therapists or medical professionals as "normal"

or "at-risk." The model may use these examples to learn biomechanical norms, such as optimal running posture, across a range of activities such as running, squatting, or jumping.

The machine learning model may employ convolutional neural networks (CNNs), recurrent neural networks (RNNs), or transformer-based architectures to extract both spatial and temporal features from the input data. By comparing incoming motion and muscle activation signals against its internal representations of normative patterns, the model may identify deviations that suggest inefficiency, fatigue, compensation, or other risk factors.

In step 504, the system may identify an abnormal or inefficient movement pattern based on the processed sensor data. These patterns may include asymmetrical gait, delayed muscle recruitment, excessive joint angles, or high-impact loading behaviors. For example, if IMU data indicates lateral knee valgus during landing and EMG data shows insufficient hamstring activation, the system may flag this combination as indicative of increased ACL injury risk or faulty rehabilitation mechanics.

In step 506, the machine learning model may be adapted using user-specific data gathered during continued use. This personalization may involve fine-tuning the model weights, updating user baselines, or clustering movement data by user profile. In one embodiment, the model may employ transfer learning to incorporate generic movement knowledge from a pre-trained model and refine it with a smaller dataset collected from the specific user. In another embodiment, the system may incorporate federated learning, where updates to the model are computed locally on the user's device to preserve privacy while still benefiting from population-wide performance improvements.

In step 508, the system may output a movement recommendation or rehabilitation instruction via a graphical user interface (GUI). The GUI may be displayed on a paired smartphone, tablet, or computer, or projected via augmented reality goggles. Output recommendations may include suggested corrective exercises, posture cues, rest periods, or reminders to slow down movement speed. For rehabilitation use cases, the GUI may track user progress over time and provide motivational goals or visualizations such as trend charts or real-time joint angle animations. The recommendations may be updated continuously as the system collects more data and learns the user's evolving biomechanics.

The method shown in FIG. 5 may operate in conjunction with other real-time injury prediction and actuation subsystems described in the present disclosure. In some embodiments, this method may also be deployed in a telemedicine or remote physical therapy setting, where a clinician remotely reviews system-generated feedback to inform ongoing treatment plans.

FIG. 6 illustrates a method 600 that may be implemented by a knee brace system to help prevent anterior cruciate ligament (ACL) injury through sensor-based monitoring, machine learning analysis, and real-time user feedback. The method may be performed by onboard electronics integrated into the knee brace or by a companion computing device such as a smartphone, tablet, or laptop.

At step 602, the system may receive motion data from at least one inertial measurement unit (IMU) sensor and neuromuscular activity data from at least one electromyography (EMG) sensor. The IMU sensor may include accelerometers, gyroscopes, and magnetometers configured to detect linear acceleration, angular velocity, and orientation. These sensors may be positioned on upper and lower segments of the brace to capture relative motion across the knee joint. The EMG sensors may be surface-mounted on muscle groups surrounding the knee, such as the quadriceps, hamstrings, or gastrocnemius, and may detect electrical signals produced during muscle activation. Preprocessing, such as filtering through butterworth filters or normalization, will be performed to enhance signal clarity and suppress sensor noise.

At step 604, the sensor data may be analyzed using a machine learning model trained to recognize movement patterns associated with increased risk of ligament injury. The model may be implemented using neural network architectures, such as convolutional neural networks (CNNs), recurrent neural networks (RNNs), or long short-term memory (LSTM) networks, which may be selected based on application requirements. The analysis may also include dimensionality reduction, feature extraction, or signal transformation techniques. The model may be trained using labeled datasets of known injury-prone movements or unsupervised methods for anomaly detection. In some cases, the system may employ transfer learning to adapt pre-trained models to a specific user or activity.

At step 606, the system may generate a prediction indicating whether the user is likely to experience a high-risk movement. This prediction may be based on kinematic thresholds, learned features, or a statistical assessment of injury likelihood. For example, the system may determine that a pivoting motion with low muscle activation presents an elevated risk of ACL strain. The prediction may be updated in real time, using a sliding time window of data, allowing the system to respond to evolving biomechanical states.

At step 608, in response to the prediction, the system may generate a feedback signal. The feedback signal may be tailored based on the level of risk, user preferences, or environmental context. The feedback may be used to prompt the user to alter their movement, slow down, or halt an activity. In some embodiments, different types of alerts— visual, auditory, or haptic—may be used individually or in combination to maximize effectiveness.

At step 610, the feedback signal may be transmitted to a feedback interface. This interface may include a visual indicator on the brace, such as an LED, a haptic motor providing vibration, or an audio module producing a tone. Alternatively or additionally, the signal may be sent wirelessly to a connected computing device for display on a graphical user interface. The user may review risk alerts, sensor data visualizations, or recommendations in real time or as part of a post-activity summary. The feedback mechanism may be adjustable over time to reflect user progress or rehabilitation goals.

The steps of the method 600 may be performed continuously during activity or triggered under certain conditions, such as elevated acceleration or joint torque. The machine learning model may be updated periodically to reflect ongoing use and may incorporate user-specific data to improve accuracy. When combined with actuator elements described elsewhere in the specification, this method may optionally coordinate predictive feedback with active force redistribution, further reducing the risk of ligament injury.

FIG. 7 illustrates a method 700 for preventing ligament injury using a wearable knee brace equipped with a hybrid actuation system and real-time biomechanical sensing. The method may be implemented by embedded processors within the brace or through a combination of on-device and mobile computing resources.

In step 702, the system receives real-time biomechanical data from at least one inertial measurement unit (IMU) sensor and at least one electromyography (EMG) sensor disposed on the knee brace. The IMU sensor may include a tri-axial accelerometer, gyroscope, and magnetometer configured to measure linear acceleration, angular velocity, and rotational orientation. The sensor may be mounted to both femoral and tibial segments of the brace to capture relative motion across the knee joint. Simultaneously, EMG sensors placed on the user's quadriceps, hamstrings, or gastrocnemius muscles detect neuromuscular activity by recording electrical signals generated during muscle contraction. These raw signals may be digitized, filtered, and normalized for downstream processing.

In step 704, the biomechanical data is analyzed using a machine learning model trained to detect movement patterns indicative of elevated ligament injury risk. The model may include convolutional neural networks (CNNs) to extract spatial features from sensor streams and long short-term memory (LSTM) networks to capture temporal dependencies in muscle activation and joint kinematics. For example, the model may learn that rapid knee abduction with insufficient hamstring recruitment corresponds to increased anterior cruciate ligament (ACL) loading. The model may be pretrained using annotated motion capture data and refined through on-device personalization or federated learning to improve performance for individual users.

In step 706, the system predicts a high-risk movement pattern likely to result in excessive ligament loading. This prediction may involve thresholding confidence scores from the model or identifying known biomechanical signatures associated with ACL strain, such as rapid internal tibial rotation or excessive anterior translation. The prediction step may be executed at a high frequency (e.g., every 100 ms) to ensure near-instantaneous intervention.

In step 708, the system determines that an actuation response is required based on the high-risk prediction. This step may include verifying the persistence or intensity of the risky movement to avoid false positives, as well as checking contextual factors such as current activity type or user-specific thresholds.

In step 710, a first actuator is activated. This actuator is configured to produce a high-force, low-displacement mechanical response, such as through piezoelectric or shape-memory alloy components. The actuator may pre-tension cross-straps, cinch down on lateral supports, or dynamically increase resistance across a jointed brace hinge. The primary objective of this actuation is to rapidly reduce rotational shear or anterior tibial translation before ligament failure occurs. The actuator may complete its response in less than 50 milliseconds and return to a neutral state once the high-risk condition resolves.

In step 712, a second actuator is activated to deliver a lower-force, higher-displacement response. This actuator may comprise a pneumatic chamber, soft robotic bladder, or servo-driven cable that adjusts the overall alignment or tension profile of the brace. Unlike the first actuator, the second actuator may remain active for an extended duration to sustain load redistribution, correct joint alignment, or offload muscle groups under strain. In some embodiments, the second actuator may inflate a lateral or posterior support structure, or gradually guide the knee through a safe movement arc to mitigate residual risk.

In step 714, a control module coordinates the operation of both actuators. This module may assign priorities based on the predicted severity of the movement, historical injury risk, user preferences, or contextual variables such as fatigue or terrain. In some embodiments, a multi-stage control algorithm may be used, where the system first attempts feedback-only alerts (e.g., vibration or auditory warnings), then escalates to partial actuation, and finally deploys the full hybrid response if risk persists. Timing synchronization may also be optimized to prevent antagonistic force outputs and ensure smooth transitions between actuators.

This hybrid response strategy allows the brace to balance speed, strength, and biomechanical precision across a wide range of movement conditions, enabling both real-time injury prevention and longer-term joint stabilization.

Figure 8:
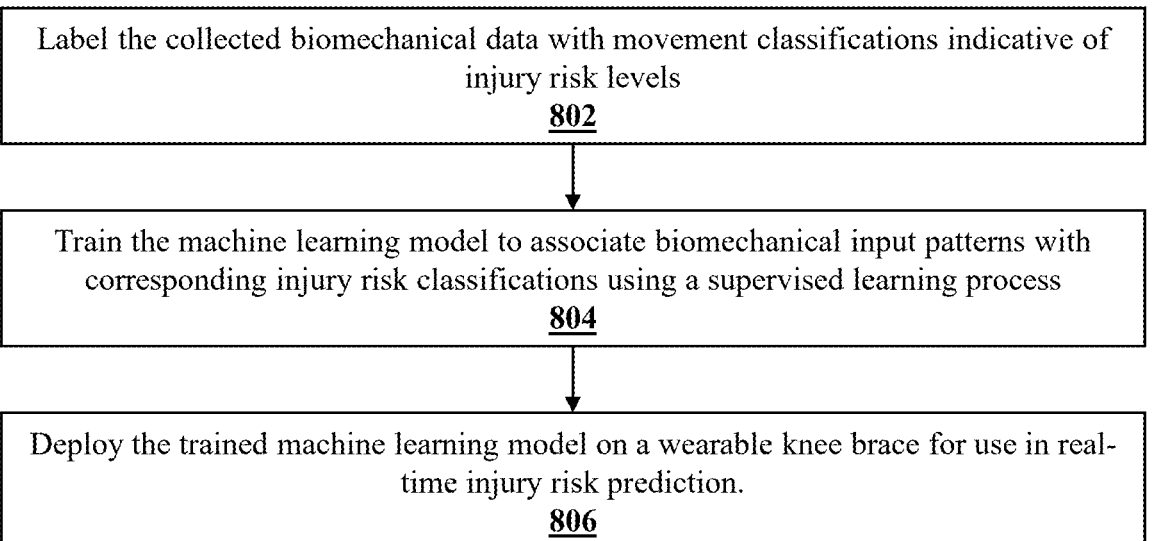
FIG. 8 is a flowchart depicting a method for training a supervised machine learning model to classify movement patterns based on labeled biomechanical data.

FIG. 8 illustrates a method 800 for training and deploying a machine learning model to classify movement patterns associated with ligament injury risk, using supervised learning and wearable sensor data. The method may be implemented using a combination of offline computing resources and embedded systems integrated into a wearable knee brace.

In step 802, biomechanical data is collected from a population of users performing various physical activities, such as walking, squatting, jumping, cutting, or pivoting. The data may be gathered using wearable sensors including inertial measurement units (IMUs) and surface electromyography (EMG) sensors. IMU signals may include linear acceleration, angular velocity, and joint orientation, while EMG signals may reflect electrical activity of muscle groups surrounding the knee, such as the quadriceps, hamstrings, and gastrocnemius. The data may be segmented into time windows (e.g., 200 to 1000 milliseconds) and synchronized across sensor modalities.

Each segment of data may be labeled with a movement classification reflecting its associated injury risk level. Labels may be generated by biomechanic experts or physical therapists based on video review, force plate analysis, or comparison to known high-risk movement patterns. Labels may include classifications such as "low risk," "moderate risk," or "high risk," or may correspond to specific joint loading thresholds. In some embodiments, automated labeling systems using external motion capture or wearable ground truth sensors may be employed to assist in the annotation process.

In step 804, the labeled biomechanical data is used to train a machine learning model using a supervised learning process. The model may include a combination of convolutional neural networks (CNNs) for spatial feature extraction and long short-term memory (LSTM) layers for temporal sequence modeling. Training may be conducted using stochastic gradient descent or a variant such as Adam, with backpropagation used to update network weights. Data augmentation techniques—such as noise injection, time-warping, and mirror transformations—may be employed to improve generalization. In some cases, the training pipeline may include dimensionality reduction (e.g., via principal component analysis) or feature selection based on mutual information or statistical relevance. The trained model may output probability scores or class predictions indicating the likelihood that an input sequence corresponds to a movement pattern with elevated ligament injury risk.

In step 806, the trained machine learning model is deployed onto a wearable knee brace for real-time use. Deployment may involve compressing or quantizing the model to enable efficient inference on a low-power embedded processor within the brace. Alternatively, the model may be deployed to a mobile device paired with the brace via Bluetooth® or another wireless protocol. During operation, the brace continuously collects IMU and EMG data, segments it in real time, and feeds the data to the deployed model. When a high-risk movement is detected, the brace may trigger a corresponding response, such as issuing a haptic warning, generating visual or audio feedback, or engaging an actuator to modify joint mechanics.

This method enables the knee brace to serve as an intelligent, context-aware injury prevention system that evolves from curated biomechanical datasets and operates autonomously in real-world athletic or rehabilitative environments.

FIG. 9 illustrates a method 900 for adapting a machine learning model to an individual user by fine-tuning a pretrained model using user-specific biomechanical data collected from a wearable knee brace. This personalized training process allows the system to account for unique anatomical, neuromuscular, and movement characteristics, thereby improving prediction accuracy and responsiveness for injury risk detection.

In step 902, the system is initialized with a machine learning model that has been pretrained on biomechanical datasets collected from a diverse population of users. The pretrained model may include layers trained on labeled sensor data—such as IMU and EMG signals—corresponding to a wide range of movements and injury risk levels. The model architecture may include convolutional layers for spatial pattern recognition and recurrent or transformer-based layers to capture temporal dependencies in time-series movement data. This general model forms the foundation for transfer learning and is designed to operate across users and activity types.

In step 904, user-specific sensor data is collected during the individual's use of the knee brace. The sensors may include at least one inertial measurement unit (IMU) and at least one surface electromyography (EMG) sensor. The IMU may be used to capture linear acceleration, angular velocity, and knee joint orientation, while the EMG sensor may capture muscle activation signals from the user's quadriceps, hamstrings, and other relevant muscle groups. This data may be collected passively during normal brace usage, or during specific onboarding sessions designed to optimize calibration.

In step 906, the system identifies calibration activities performed by the user while wearing the brace. These activities may include walking, jumping, squatting, or pivoting, each selected to represent biomechanical conditions relevant to ACL or PCL strain. The system may prompt the user via a connected application to perform one or more movement trials, during which synchronized IMU and EMG data is recorded. Activity detection may be performed using template-matching, signal segmentation, or threshold-based classification to ensure high-quality input during the calibration phase.

In step 908, the pretrained model is fine-tuned using the user-specific sensor data to generate a personalized model. Fine-tuning may involve updating model weights through additional training epochs, adjusting bias parameters, or modifying layer-specific learning rates. In some embodiments, only the final layers of the model may be updated, while earlier layers remain frozen to preserve general motion features. The training process may be conducted on-device or offloaded to a paired mobile device or cloud-based server, depending on available computational resources and privacy constraints. The fine-tuned model becomes personalized to the user's baseline joint mechanics, muscle firing patterns, and movement tendencies.

In step 910, the personalized model is deployed to the knee brace or paired computing device and used to analyze real-time biomechanical data. The model continuously monitors the incoming IMU and EMG data during dynamic activity and applies the learned risk classification or regression function to detect potentially injurious movement patterns. The personalized model may outperform the base model by reducing false positives and increasing sensitivity to subtle deviations in the user's normal movement profile, thereby enabling more accurate and timely interventions through feedback or actuation.

This method allows the knee brace system to adapt to a wide variety of users with differing anatomy, gait characteristics, and injury histories. By incorporating user-specific personalization, the system achieves a higher level of biomechanical intelligence and clinical relevance for real-world injury prevention.

FIG. 10 illustrates a method 1000 for training a machine learning model across a network of wearable knee brace devices using federated learning, a decentralized training approach that enables collaborative model improvement without requiring direct transmission of raw user data. This approach preserves user privacy while allowing the system to generalize across diverse populations and activity profiles.

In step 1002, each knee brace independently trains a local machine learning model using biomechanical sensor data collected during use. Each brace may include at least one inertial measurement unit (IMU) and one electromyography (EMG) sensor configured to capture motion and neuromuscular activity. As the user wears the brace during activities such as walking, jumping, or pivoting, the brace records time-series IMU and EMG data and uses it to refine a copy of the shared model architecture. The training process may occur locally using an embedded processor or an associated mobile device. During local training, the model may update its weights using a stochastic gradient descent algorithm or a privacy-preserving optimization method, such as differentially private stochastic gradient descent (DP-SGD).

In step 1004, the updated model parameters—such as weight gradients or partial weight matrices—are transmitted to a central server. Importantly, raw sensor data, which may contain sensitive biometric or movement information, is not transmitted. Instead, only the computed updates are shared. Each local update may be encrypted or anonymized using secure aggregation protocols before transmission. This ensures that individual users' data remains confidential and compliant with privacy regulations.

In step 1006, the central server receives model updates from multiple knee brace devices and aggregates them to produce a new global model. Aggregation may be performed using federated averaging, where each update is weighted based on local dataset size or validation performance. The server may also discard outlier updates or apply regularization techniques to prevent model drift. The resulting global model reflects knowledge learned from a broad population of users, encompassing a wide variety of movement styles, anatomical features, and injury risk factors.

In step 1008, the updated global model is distributed back to the participating knee brace devices. Each device receives the refined model, which may be used to replace the local model or further fine-tune it through additional personalization. Once deployed, the global model may be used in real time to analyze incoming biomechanical data and predict ligament injury risk during activity. The federated learning cycle may repeat periodically, such as daily or weekly, depending on system settings and network availability.

This federated learning architecture enables the knee brace system to continuously improve its machine learning model over time while safeguarding user privacy and minimizing bandwidth consumption. The resulting model is robust, adaptable, and capable of recognizing high-risk movement patterns across diverse users and contexts without relying on centralized data storage.

While various embodiments of the present invention have been described in detail, it will be appreciated by those skilled in the art that modifications, substitutions, and variations may be made without departing from the spirit or scope of the invention. The methods, systems, components, and architectures described herein are intended to be illustrative and non-limiting. Features described in connection with one embodiment may be used with other embodiments, and not all features of all embodiments need be implemented together.

The processes and methods described herein may be implemented using hardware, software, or a combination of both. In certain embodiments, the machine learning models, control logic, signal processing algorithms, and actuation coordination routines may be executed by one or more processors configured to carry out instructions stored on a computer-readable medium. Such a medium may include, for example, random-access memory (RAM), read-only memory (ROM), flash memory, magnetic storage media, optical storage media, or any other non-transitory computer-readable storage medium.

Accordingly, the invention is not to be limited by the specific illustrative embodiments described above, but rather is to be defined by the scope of the claims and any equivalents thereto.

What is claimed is:

1. A method for preventing anterior cruciate ligament injury in a user wearing a knee brace, comprising:
    receiving motion data from at least one inertial measurement unit (IMU) sensor and neuromuscular activity data from at least one electromyography (EMG) sensor positioned on the user's leg;
    analyzing the motion data and neuromuscular activity data using a machine learning model trained to identify movement patterns associated with increased risk of ligament injury;
    predicting, based on the analysis, an imminent high-risk movement likely to cause excessive force on the anterior cruciate ligament;
    generating a feedback signal in response to the prediction; and
    transmitting the feedback signal to at least one of a visual, auditory, or haptic feedback device to alert the user to modify their movement.

2. The method of claim 1, wherein the machine learning model comprises a convolutional neural network (CNN), a recurrent neural network (RNN), or a long short-term memory (LSTM) network.

3. The method of claim 2, wherein the prediction is generated using a model trained on labeled datasets comprising time-series IMU and EMG data collected during movement activities such as walking, jumping, squatting, or pivoting.

4. The method of claim 1, wherein the EMG sensor is positioned over the user's hamstring muscles and the prediction is based at least in part on reduced hamstring activation during high-impact motion.

5. The method of claim 1, further comprising dynamically adjusting the feedback signal based on user response history or rehabilitation progress.

6. The method of claim 1, wherein the feedback signal is delivered via a mobile application that displays a real-time biomechanical risk score.

7. The method of claim 1, wherein the IMU comprises a tri-axial accelerometer and gyroscope configured to compute jerk, linear acceleration, and angular velocity of the user's knee joint.

8. The method of claim 7, wherein the IMU is positioned on both a femoral segment and a tibial segment of the knee brace to capture relative joint movement.

9. The method of claim 1, wherein the steps are implemented using instructions stored on a non-transitory computer-readable medium and executed by at least one processor integrated into the knee brace system.

10. A method for dynamically reducing knee joint loading in a wearable brace, comprising:

detecting, using at least one IMU sensor on a knee brace, relative motion between a femoral attachment point and a tibial attachment point;

detecting, using at least one EMG sensor, muscle activation levels in at least one of the quadriceps, hamstring, or gastrocnemius muscles;

comparing the detected motion and muscle activation to one or more predetermined thresholds indicative of excessive force or torque on the anterior cruciate ligament;

generating a control signal in response to detecting a value that exceeds the threshold; and activating one or more actuators coupled to the knee brace to apply tension to at least one strap or artificial muscle, thereby offloading force from the knee joint.

11. The method of claim 10, wherein the one or more actuators comprise a piezoelectric actuator configured to apply high-force, low-displacement tension.

12. The method of claim 11, wherein the one or more actuators further comprise a pneumatic actuator configured to apply low-force, high-displacement movement correction.

13. The method of claim 10, wherein the control signal is generated based on detecting anterior tibial translation exceeding a defined threshold in conjunction with insufficient muscle activation.

14. The method of claim 10, further comprising deactivating the actuator after a predetermined duration or upon resolution of the high-risk condition.

15. The method of claim 10, wherein the prediction and actuator activation are performed in real time with a latency of less than 100 milliseconds.

16. A method for dynamically reducing knee joint loading in a wearable brace, comprising: detecting, using at least one IMU sensor on a knee brace, relative motion between a femoral attachment point and a tibial attachment point; detecting, using at least one EMG sensor, muscle activation levels in at least one of quadriceps, hamstring, or gastrocnemius muscles; comparing the detected motion and muscle activation to one or more predetermined thresholds indicative of excessive force or torque on the anterior cruciate ligament; generating a control signal in response to detecting a value that exceeds the threshold; and activating one or more actuators coupled to the knee brace to apply tension to at least one strap or artificial muscle, thereby offloading force from the knee joint.

17. The method of claim 16, wherein the movement recommendation includes a corrective exercise to improve joint stability or muscle coordination.

18. The method of claim 17, wherein the graphical user interface displays a trend analysis of the user's joint angles or muscle activation patterns over time.

19. The method of claim 16, wherein the model adapts using a transfer learning process that fine-tunes model parameters based on calibration movements performed by the user.

20. The method of claim 19, wherein the machine learning model is further refined using a federated learning framework that aggregates encrypted model updates from multiple devices without sharing raw data.

* * * * *